(12) United States Patent
Roberts et al.

(10) Patent No.: US 8,394,411 B2
(45) Date of Patent: Mar. 12, 2013

(54) PAPILLOMAVIRUS PSEUDOVIRUSES FOR DETECTION AND THERAPY OF TUMORS

(75) Inventors: Jeff Roberts, Rockville, MD (US); Douglas R. Lowy, Bethesda, MD (US); John T. Schiller, Kensington, MD (US)

(73) Assignee: The United States of America as represented by the Secretary, Dept. of Health and Human Services National Institutes of Health, Washington, DC (US)

( * ) Notice: Subject to any disclaimer, the term of this patent is extended or adjusted under 35 U.S.C. 154(b) by 344 days.

(21) Appl. No.: 12/598,684

(22) PCT Filed: May 1, 2008

(86) PCT No.: PCT/US2008/062296
§ 371 (c)(1),
(2), (4) Date: Feb. 8, 2010

(87) PCT Pub. No.: WO2008/140961
PCT Pub. Date: Nov. 20, 2008

(65) Prior Publication Data
US 2010/0135902 A1     Jun. 3, 2010

Related U.S. Application Data

(60) Provisional application No. 60/928,495, filed on May 8, 2007, provisional application No. 61/065,897, filed on Feb. 14, 2008.

(51) Int. Cl.
| | |
|---|---|
| *A61K 9/14* | (2006.01) |
| *A61K 9/51* | (2006.01) |
| *A61K 48/00* | (2006.01) |
| *A61K 51/02* | (2006.01) |
| *A61K 51/12* | (2006.01) |
| *A61K 39/12* | (2006.01) |

(52) U.S. Cl. .... 424/489; 424/499; 424/93.2; 424/199.1; 424/1.17

(58) Field of Classification Search .................. None
See application file for complete search history.

(56) References Cited

U.S. PATENT DOCUMENTS

| | | | | |
|---|---|---|---|---|
| 6,416,945 | B1 * | 7/2002 | McCarthy et al. | 435/5 |
| 6,420,160 | B1 * | 7/2002 | Bloch | 435/239 |
| 2005/0142115 | A1 | 6/2005 | Qiao et al. | |

OTHER PUBLICATIONS

Gardasil package insert, Merck & Co., Inc., Jun. 2006.*
Sigma-Aldrich 2002-2003 catalog, p. 1562.*
Malboef et al (Vaccine 25:3270-3276, 2007).*
Nieland et al (Journal of Cellular Biology 73:145-152, 1999).*
International Search Report prepared by the European Patent Office on May 7, 2009, for International Application No. PCT/US2008/062296.
Nieland J D et al. "Chimeric Papillomavirus-Like Particles Induce a Murine Self-Antigen-Specific Protective and Therapeutic Antitumor Immune Response." Journal of Cellular Biochemistry, Wiley-Liss Inc., US, vol. 73, No. 2, May 1, 1999, pp. 145-152.
Schiller J T et al. "Papillomavirus-Like Particle Based Vaccines: Cervical Cancer and Beyond." Expert Opinion on Biological Therapy, Ashley, London, GB, vol. 1, No. 4, Jul. 1, 2001, pp. 571-581.
Cho Cheong-Weon et al. "Improvement of Gene Transfer to Cervical Cancel Cell Lines Using Non-Viral Agents." Cancer Letters, vol. 162, No. 1, Jan. 10, 2001, pp. 75-85.
Touze A et al. "In vitro gene transfer using human papillomavirus-like particles." Nucleic Acids Research, Oxford University Press, Surrey, GB, vol. 5, No. 26, Mar. 1, 1998, pp. 1317-1323.
Da Silva Diane M et al. "Physical Interaction of Human Papillomavirus Virus-Like Particles with Immune Cells." International Immunology, vol. 13, No. 5, May 2001, pp. 633-641.

* cited by examiner

*Primary Examiner* — Mary E Mosher
(74) *Attorney, Agent, or Firm* — Sheridan Ross P.C.; Gary J. Connell; Richard J. Stern

(57) ABSTRACT

Disclosed herein are methods of detecting tumors, monitoring cancer therapy, and selectively inhibiting the proliferation and/or killing of cancer cells utilizing a papilloma pseudovirus or a papilloma virus-like particle (VLP).

9 Claims, 14 Drawing Sheets

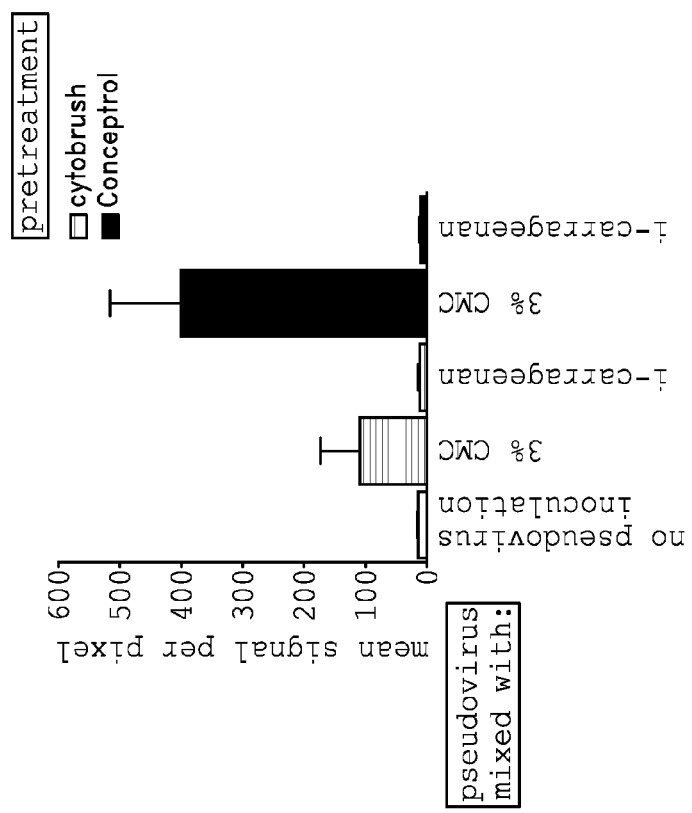
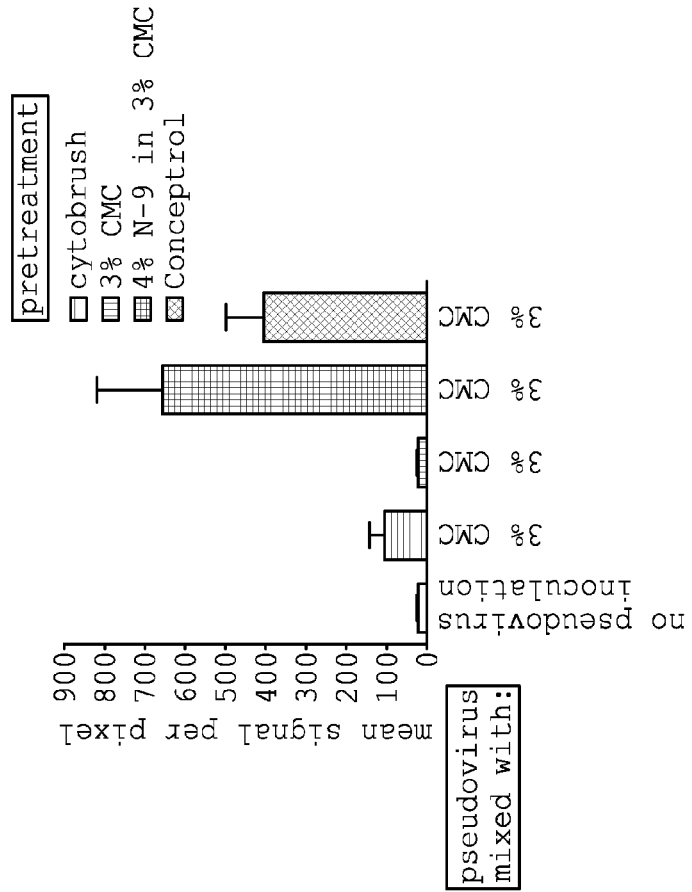

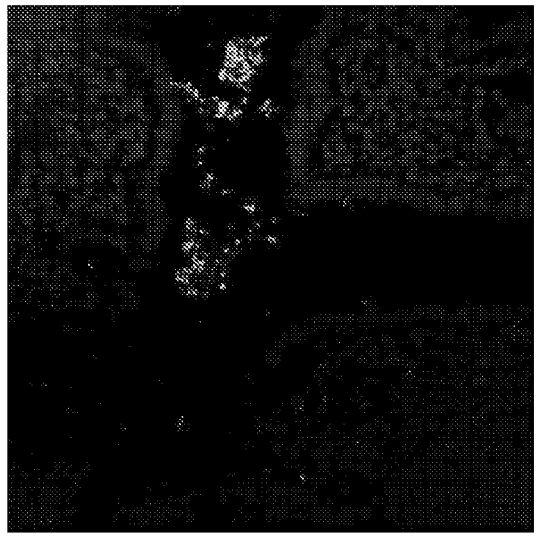
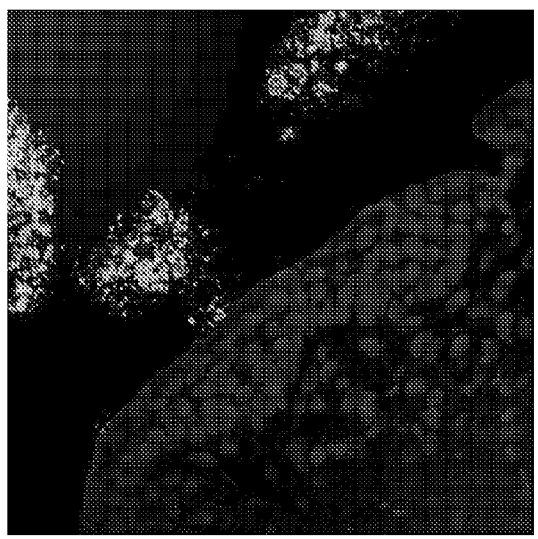
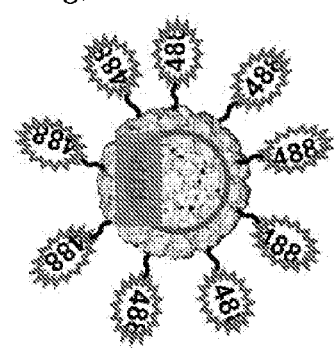
green = (infectious) dye-coupled HPV capsids
HPV capsids do not bind apical surfaces of intact epithelium
FIG. 4

HPV16-GFP Infection is Specific for Tumor Tissue

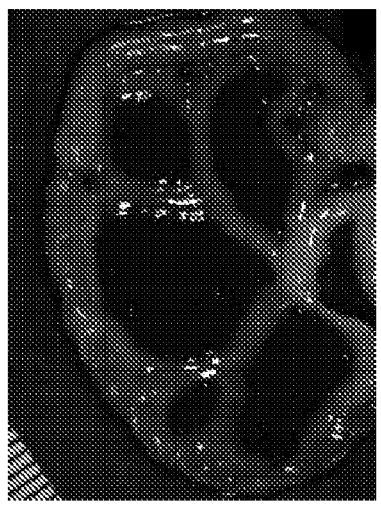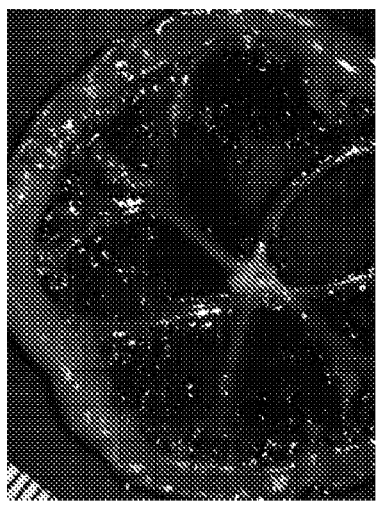
FIG. 12 HPV16-RFP Targets SKOV3 In Vivo Tumor-bearing mice were injected with $2 \times 10^4$ TC-1 cells IV 2wks prior to the expt. This is an established protocol for producing lung metastases. The +psv groups received $\sim 1 \times 10^7$ HPV16-luciferase psv IV. No signal was detectable in the tumor-free mouse that received psv IV-administered pseudovirus targets lung metastases

SEQUENCE LISTING

<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: Oligo T Primer A

<400> SEQUENCE: 1
gcggcgtcta gaattttttt tttttttttt tttttttttt tttttttttt tttttttt      59

<210> SEQ ID NO 2
<211> LENGTH: 59
<212> TYPE: DNA
<213> ORGANISM: Artificial Sequence
<220> FEATURE:
<223> OTHER INFORMATION: Oligo T Primer B

<400> SEQUENCE: 2
gcggcgtcta gaaaaaaaaa aaaaaaaaaa aaaaaaaaaa aaaaaaaaaa aaaaaaaa      59

PAPILLOMAVIRUS PSEUDOVIRUSES FOR DETECTION AND THERAPY OF TUMORS

CROSS REFERENCE TO RELATED APPLICATIONS

This application is a national stage application under 35 U.S.C. 371 of PCT Application No. PCT/US2008/062296 having an international filing date of 1 May 2008, which designated the United States, which PCT application claimed the benefit of priority to U.S. Provisional Application Nos. 60/928,495 filed May 8, 2007, and 61/065,897 filed Feb. 14, 2008, the entire disclosure of each of which are hereby incorporated herein by reference.

REFERENCE TO SEQUENCE LISTING

This application contains a Sequence Listing submitted as an electronic text file named "nih360001vpcseq.txt" having a size in bytes of 1 KB, and created on Sep. 22, 2009. The information contained in this electronic file is hereby incorporated by reference in its entirety pursuant to 37 CFR §1.52 (e)(5).

FIELD OF THE INVENTION

This invention relates to the fields of molecular biology and medicine. More specifically, disclosed herein are methods for detecting tumors and treating subjects suffering from cancer using papilloma pseudoviruses and virus-like particles (VLPs).

BACKGROUND OF THE INVENTION

Cancer is diagnosed in more than 1 million people every year in the United States alone. In spite of numerous advances in medical research, cancer remains the second leading cause of death in the United States, accounting for roughly 1 in every four deaths. Although numerous treatments are available for various cancers, many forms of cancer remain uncurable, untreatable, and/or become resistant to standard therapies. For example, tumors may be inoperable because of their location or they may metastasize, making it difficult or impossible to treat the disease. Current therapies have considerable shortcomings. For instance, radiation therapy can cause damage to epithelial surfaces, swelling, infertility, fatigue, fibrosis, hair loss, dryness, and cancer. Chemotherapy can induce nausea, vomiting, diarrhea, constipation, anemia, malnutrition, hair loss, memory loss, depression of the immune system and hence infections and sepsis, hemorrhage, secondary neoplasms, cardiotoxicity, hepatotoxicity, nephrotoxicity, and otoxicity. Clearly the need for robust techniques to diagnose and treat cancer is manifest Viruses have been shown to have tremendous utility in a variety of biomedical applications. Many of these techniques take advantage of the unique ability of viruses to enter cells at high efficiency. Some of these applications exploit viral gene expression and replication to induce expression of an inserted heterologous gene. It is well known that a variety of viruses deliver and express genes in cells (either viral or other genes), which may be useful, for example, in gene therapy, the development of vaccines, or cancer biology.

There is extensive literature on the use of viral vectors, particularly those based on adenovirus, adeno-associated virus (AAV), herpes virus and retrovirus, to increase the potency of anti-tumor therapy, however, these methodologies are in their infancy.

SUMMARY OF THE INVENTION

Embodiments disclosed herein relate to methods for detecting the presence of cancer cells, (e.g., a tumor cell), bound to at least one papilloma pseudovirus (PsV) or papilloma virus-like particle (VLP). Some approaches involve identifying a subject having or suspected of having cancer cells, administering to the subject a detectable amount of a papilloma pseudovirus or VLP that comprises a detectable label, and detecting the presence or absence of cancer cells bound to the papilloma pseudovirus or VLP that comprises the detectable label. In some embodiments, the label is chemically coupled to the pseudovirus or VLP. In other embodiments, the presence, absence, or amount of papilloma pseudovirus or VLP bound to cancer cells and the presence, absence, or amount of papilloma pseudovirus or VLP bound to normal cells is measured. In more embodiments, the pseudovirus comprises a gene encoding a label (e.g., luciferase or GFP). Other labels, including fluorescent, radioactive, or chemiluminscent labels, which can be incorporated in or coupled to the PsV or VLP, are also contemplated for use with some embodiments.

Further embodiments disclosed herein relate to methods for monitoring a cancer therapy in a subject including identifying a subject with a cancer, providing the subject a cancer therapy, administering to the subject a detectable amount of a papilloma pseudovirus or VLP that comprises a detectable label, and determining the presence or amount of PsV or VLP bound to cancer cells in the subject after, or during the course of the treatment with the cancer therapy. By using successive inoculations with fluorescently labeled PsV or VLP, for example, real time efficacy of the particular therapy over time can be evaluated. In some embodiments, the label is chemically coupled to the pseudovirus or VLP. In other embodiments, the presence or amount of papilloma pseudovirus or VLP bound to the cancer cells and the presence or amount of papilloma pseudovirus or VLP bound to normal cells is measured. In some embodiments, the pseudovirus includes a gene encoding the label or, optionally, a therapeutic nucleic acid (e.g., an oligo T nucleic acid).

More embodiments disclosed herein relate to methods of selectively inhibiting the proliferation of cancer cells and/or killing cancer cells without inhibiting proliferation of and/or killing normal cells including identifying a subject with a cancer and administering to the identified subject an inhibitory amount of a composition comprising a papilloma pseudovirus or VLP and a therapeutic agent. In some embodiments, the therapeutic agent is chemically coupled to the papilloma pseudovirus or VLP. In other embodiments, the therapeutic agent is incorporated within the papilloma pseudovirus or VLP. In some embodiments, the therapeutic agent is a toxin. In some embodiments, the therapeutic agent comprises an oligo T nucleic acid. In some embodiments, the therapeutic agent comprises a radionuclide. Additional embodiments disclosed herein relate to kits that include a papilloma pseudovirus or VLP, pharmaceutical carriers, and instructions for using the kit components.

Accordingly, aspects of the invention concern methods of detecting the presence of cancer cells bound to a papilloma pseudovirus or a papilloma VLP comprising identifying a subject having or suspected of having cancer cells; administering or providing to said subject a detectable amount of a papilloma pseudovirus or a papilloma VLP that comprises a detectable label; and detecting the presence of cancer cells bound to said papilloma pseudovirus or said papilloma VLP that comprises a detectable label. In some embodiments, the label is chemically coupled to said pseudovirus or VLP or said pseudovirus comprises a gene encoding said label and in more embodiments the presence or amount of pseudovirus or VLP bound to said cancer cells and the presence or amount of pseudovirus or VLP bound to normal cells is measured. The label used in these embodiments can be fluorescent, radioactive or chemiluminescent or otherwise detectable.

Aspects of the invention also include methods for evaluating a cancer therapy comprising identifying a subject with a cancer; providing said subject a cancer therapy; administering or providing to said subject a detectable amount of a papilloma pseudovirus or papilloma VLP that comprises a detectable label; and determining the presence or amount of said pseudovirus or said VLP bound to cancer cells in said subject, before a treatment with said cancer therapy and during or after a period of said treatment. In some embodiments, the label is chemically coupled to said pseudovirus or said VLP or said psuedovirus comprises a gene encoding said label and in some embodiments, the presence or amount of said pseudovirus or said VLP bound to said cancer cells and the presence or amount of said pseudovirus or said VLP bound to normal cells is measured. The label used can be fluorescent, radioactive, chemiluminescent or otherwise detectably labeled.

Aspects of the invention also include methods of inhibiting the proliferation of cancer cells and/or killing cancer cells without inhibiting proliferation and/or killing of normal cells comprising identifying a subject with a cancer; and administering or providing to said identified subject a composition that comprises a therapeutic agent formulated with a papilloma pseudovirus or a papilloma VLP. In some embodiments, the therapeutic agent is chemically coupled to said pseudovirus or said VLP and in other embodiments the therapeutic agent is incorporated within said pseudovirus or said VLP. The therapeutic agent can be a toxin, radionuclide, ganciclovir or acyclovir, or oligo T, preferably, oligo T, of less than or equal to 200, 175, 150, 125, 100, 95, 80, 75, 70, 65, 60, 55, 50, 45, 40, 35, 30, 25, 20, 15, or 10 nucleotides. In some embodiments, the therapeutic agent is a nucleic acid expressing oligo T and said nucleic acid is operably joined to a Pol III promoter. In some embodiments the methods above are used inhibit, kill, evaluate, or diagnose the status of a cancer is selected from the group consisting of leukemia, lymphoma, myeloma, plasmacytoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, neuroglioma, and retinoblastoma.

Still more embodiments include kits comprising a papilloma pseudovirus or a papilloma VLP, a pharmaceutical carrier, and instructions for using the kit components and method of detecting the presence of cervical cancer in a subject, comprising providing to said subject a composition comprising a papilloma VLP coupled to or containing a label; removing unbound VLPs that comprise said label; and detecting the presence of cancer cells bound to said VLP that comprises said label.

In some of these embodiments, the label is chemically coupled to said VLP and in some embodiments, the presence or amount of said VLP bound to said cancer cells and the presence or amount of said VLP bound to normal cells is measured. The label can be fluorescent, radioactive, chemiluminescent or otherwise detectably labeled.

Aspects of the invention also include a composition comprising a nucleic acid that comprises an oligo T domain of at least 10 and less than or equal to 200 consecutive T residues, such as an oligo T domain consisting essentially of 45 nucleotides or an oligo T domain that consists of 45 nucleotides. These nucleic acids or nucleic acids encoding these molecules can be operably linked Pol III promoter.

BRIEF DESCRIPTION OF THE DRAWINGS

FIGS. 1a-1d. Effects of mechanical disruption, N-9 and carrageenan on HPV16 pseudovirus infection of the mouse cervicovaginal mucosa. Multispectral imaging results (representative of two or three separate experiments), expressed as mean signal per pixel, for mice (six per group) are indicated on the Y axis and gels used to prepare the pseudovirus inoculum are indicated on the X axis. Method of pretreatment is indicated by the key. Error bars represent standard error of the mean. (FIG. 1a) Comparison of the potentiation of infection by mechanical and chemical disruption. (FIG. 1b) Protection provided by carrageenan when mixed with the inoculum. (FIG. 1c) Protection provided by over-the-counter lubricants when mixed with the inoculum. (FIG. 1d) Protection provided by carrageenan when mixed with N-9 during pretreatment.

FIG. 2. Quantitative analysis of murine reproductive tract infection. Conceptrol-treated mice were mock infected (top) or challenged with HPV-16-tdTomato pseudovirus (bottom). After 3 d, the entire reproductive tract was dissected out and the ventral wall of the vagina and cervix incised sagitally.

FIG. 4. Green fluorescent dye-coupled HPV capsids bound neither the squamous or simple epithelium that lines the female mouse reproductive tract.

FIG. 12. HPV16 pseudovirus efficiently and selectively infects ovarian cancer cells implanted on the peritoneal membrane as demonstrated by multispectral fluorescence imaging.

DETAILED DESCRIPTION OF THE INVENTION

Figure 1D:
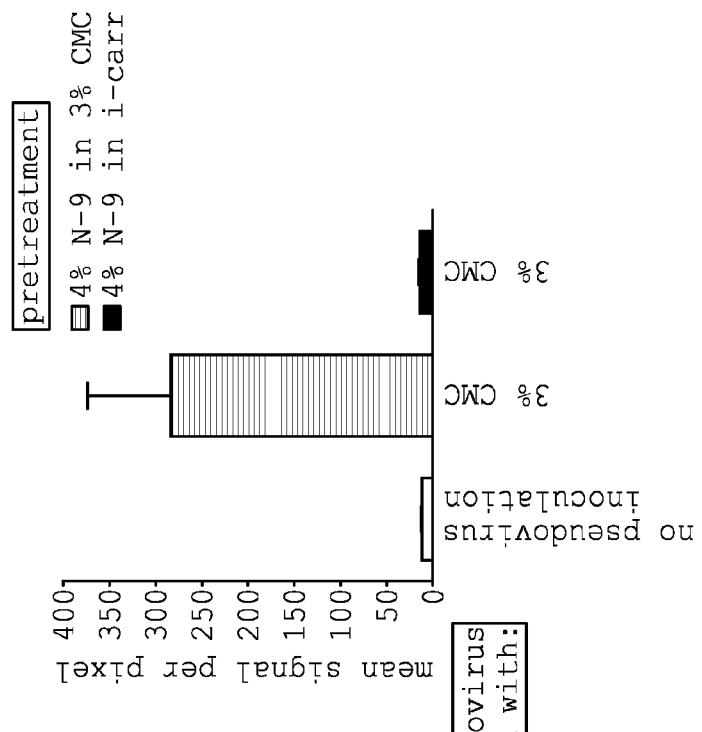

Disclosed herein is the unexpected discovery that papilloma pseudoviruses and papilloma VLPs selectively bind to and infect cancer cells but not normal cells. While not wishing to be bound to any particular theory or creating an estoppel thereby, it is contemplated that, in comparison to current viral gene transfer vectors, papilloma pseudoviruses and VLPs unexpectedly offer many benefits. Papilloma pseudoviruses and VLPs will not be become involved in competing interaction with normal cells, which can hinder the effective delivery of the viral vectors to the cancer cells. The inability of papilloma pseudoviruses and VLPs to attach to normal cells in intact tissues (e.g., untransformed or non-cancerous) will also minimize cytotoxicity of the treatment. Further, because the pseudoviruses or VLPs preferentially kill cancer cells, they will preferentially induce an immune response against the cancer cells. Lastly, pseudoviruses and/or VLPs for many papillomavirus types can be rapidly generated and papillomavirus neutralizing antibodies are type-restricted. Accordingly, neutralizing antibody-mediated inhibition and boosting with homologous papilloma pseudovirus or VLP can be overcome by use of papilloma pseudovirus or VLP of another type.

As described herein, it is intended that where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

In some contexts, the terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

In some contexts, the terms "ameliorating," "treating," "treatment," "therapeutic," or "therapy" do not necessarily mean total cure or abolition of the disease or condition. Any alleviation of any undesired signs or symptoms of a disease or condition, to any extent, can be considered amelioration, and in some respects a treatment and/or therapy. Furthermore, treatment may include acts that may worsen the patient's overall feeling of well-being or appearance.

The term "therapeutically effective amount/dose" or "inhibitory amount" is used to indicate an amount of an active compound, or pharmaceutical agent, that elicits a biological or medicinal response. This response may occur in a tissue, system, animal or human and includes alleviation of the symptoms of the disease being treated. As used herein with respect to pseudoviral vectors of the invention, the term "therapeutically effective amount/dose" refers to the amount/dose of a vector or pharmaceutical composition containing the vector that is sufficient to produce an effective anti-tumor response upon administration to a subject.

The term "nucleic acids", as used herein, may be DNA or RNA. Nucleic acids may also include modified nucleotides that permit correct read through by a polymerase and do not alter expression of a polypeptide encoded by that nucleic acid. The terms "nucleic acid" and "oligonucleotide" are used interchangeably to refer to a molecule comprising multiple nucleotides. As used herein, the terms refer to oligoribonucleotides as well as oligodeoxyribonucleotides. The terms shall also include polynucleosides (i.e., a polynucleotide minus the phosphate) and any other organic base containing polymer. Nucleic acids include vectors, e.g., plasmids, as well as oligonucleotides. Nucleic acid molecules can be obtained from existing nucleic acid sources, but are preferably synthetic (e.g., produced by oligonucleotide synthesis).

The phrase "nucleotide sequence" includes both the sense and antisense strands as either individual single strands or in the duplex.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It being further understood that the sequence includes the degenerate codons of the native sequence or sequences which may be introduced to provide codon preference in a specific host cell.

By "DNA" is meant a polymeric form of deoxyribonucleotides (adenine, guanine, thymine, or cytosine) in double-stranded or single-stranded form, either relaxed and supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence homologous to the mRNA). The term captures molecules that include the four bases adenine, guanine, thymine, or cytosine, as well as molecules that include base analogues which are known in the art.

A "gene" or "coding sequence" or a sequence, which "encodes" a particular protein, is a nucleic acid molecule which is transcribed (in the case of DNA) and translated (in the case of mRNA) into a polypeptide in vitro or in vivo when placed under the control of appropriate regulatory or control sequences. The boundaries of the gene are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

The term "operably linked" refers to an arrangement of elements, wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

The term "homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using, readily available computer programs. Alternatively, homology can be determined by hybridization of polynucleotides under conditions, which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

By "isolated" when referring to a nucleotide sequence, is meant that the indicated molecule is present in the substantial absence of other biological macromolecules of the same type. Thus, an "isolated nucleic acid molecule, which encodes a particular polypeptide," refers to a nucleic acid molecule, which is substantially free of other nucleic acid molecules that do not encode the subject polypeptide; however, the molecule may include some additional bases or moieties, which do not deleteriously affect the basic characteristics of the composition.

The terms "vector", "cloning vector", "expression vector", and "helper vector" mean the vehicle by which a DNA or RNA sequence (e.g., a foreign gene) can be introduced into a host cell, so as to promote expression (e.g., transcription and/or translation) of the introduced sequence. Vectors include plasmids, phages, viruses, pseudoviruses, etc. As used herein with respect to the pseudoviral vectors, the term "expression vector" is used most commonly to refer to a vector that is capable of infecting a host cell, while the term "helper vector" is used to refer to a vector that is able to mediate proper packaging of the "expression vector" into a virus-like particle.

"Gene transfer" or "gene delivery" refers to methods or systems for reliably inserting foreign DNA into host cells.

As used herein, the term "transfection" is understood to include any means, such as, but not limited to, adsorption, microinjection, electroporation; lipofection and the like for introducing an exogenous nucleic acid molecule into a host cell. The term "transfected" or "transformed", when used to describe a cell, means a cell containing an exogenously introduced nucleic acid molecule and/or a cell whose genetic composition has been altered by the introduction of an exogenous nucleic acid molecule.

As used herein, the term "tumor" refers to a tissue comprising transformed cells that grow uncontrollably. A tumor may be benign (benign tumor) or malignant (malignant tumor or cancer). Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, neuroglioma, and retinoblastoma.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

As used herein, the term "heterologous sequence or gene" means a nucleic acid (RNA or DNA) sequence, which is not naturally found in association with the nucleic acid sequences of the specified molecule, e.g., a papillomavirus genome. The section below provides greater detail on some approaches that can be used to prepare virus-like particles and pseudoviruses.

Virus-Like Particles and Pseudovirus Preparation

The term "virus-like particle" ("VLP") refers to an organized structure comprising self-assembling ordered arrays of one or more viral capsid proteins that do not include a viral genome. For example, VLPs having papillomavirus L1 capsid protein alone, or having both L1 and L2 capsid proteins together can be prepared. The methods used to prepare recombinant capsid particles for many papillomaviruses are known in the art. Some approaches are described, for example, in U.S. Patent Publication No. 2006/0269954, which is hereby expressly incorporated by reference in its entirety.

The term "recombinant protein" refers to a protein that is produced using molecular biology techniques, for example, recombinant DNA technology. As an example, "recombinant protein" can refer to a protein from a genetically engineered nucleic acid, such as a "recombinant nucleic acid construct." Any protein, peptide, or polypeptide can be encoded by an engineered nucleic acid construct or recombinant nucleic acid construct. The term "protein expression" refers to the processes of transcription and translation of nucleic acids to produce polypeptides.

"Pseudoviruses" or "papilloma pseudoviruses" or "papillomavirus gene transfer vectors" refer to one or more papillomavirus capsid proteins that assemble and package heterologous nucleic acids (e.g., DNA) with or without viral nucleic acids (e.g., DNA) into infectious particles. The methods used to produce papilloma pseudoviruses are known in the art and are described, for example, in U.S. Pat. Nos. 6,599,739, 7,205,126, and 6,416,945; and in Buck and Thomspon, Production of Papillomavirus-Based Gene Transfer Vectors. Current Protocols in Cell Biology 26.1.1-26.1.19, December 2007, all of which are hereby expressly incorporated by reference in their entireties.

The term "capsomeric structure" or "capsid" or "capsid particle" includes VLPs and pseudoviruses. The following section describes some of the diagnostic embodiments contemplated.

Diagnostics

Some embodiments disclosed herein relate to methods for detecting the presence of cancer cells bound to papilloma pseudovirus or papilloma VLP. Some approaches involve identifying a subject having or suspected of having cancer cells, administering to the subject a detectable amount of a papilloma pseudovirus or VLP that comprises a detectable label, and detecting the presence of cancer cells bound to a papilloma pseudovirus or VLP that comprises a detectable label.

Other embodiments disclosed herein relate to methods for detecting the presence of pre-malignant conditions (e.g., dysplasia or hyperproliferative disease). Some approaches involve identifying a subject having or suspected of having a pre-malignant condition, administering to the subject a detectable amount of a papilloma pseudovirus or VLP that comprises a detectable label, and detecting the presence of pre-malignant cells bound to a papilloma pseudovirus or VLP that comprises a detectable label.

Embodiments disclosed herein relate to methods to identify all kinds of cancers, tumors, metastases, and pre-malignant conditions (e.g., dysplasia or hyperproliferative disease). While not being bound to any particular theory, it is believed that the papilloma pseudovirus or VLP selectively binds to and delivers the label to cancer cells without binding to normal cells in intact tissues, where the number of normal cells in intact tissues bound to the pseudovirus or VLP are less than or equal to 10%, 9%, 8%, 7%, 6%. 5%, 4%, 3%, 2%, 1%, 0.5%, 0.4, 0.3%, 0.2%, 0.1%, 0.09%, 0.08%, 0.07%, 0.06%, 0.05%, 0.04%, 0.03%, 0.02%, or 0.01% of the total number of cells bound by the pseudovirus or VLP.

The detectable label can be a reporter gene carried within the papilloma pseudovirus or a label chemically coupled to a capsid protein of the papilloma pseudovirus or VLP.

Reporter Genes

Since papilloma pseudoviral vectors are gene transfer vectors, it is contemplated that the cancer cells can be selectively labeled with reporter genes that are incorporated in the pseudovirus. As used herein a "reporter" or a "reporter gene" refers to a nucleic acid molecule capable of being transcribed as mRNA when operatively linked to a promoter, except that the term "reporter gene" as used herein, is not intended to include wild-type papillomavirus sequences. Preferred reporter genes include luciferase (e.g., firefly luciferase or Renilla luciferase), βgalactosidase, chloramphenicol acetyl transferase (CAT), thymidine kinase (TK), and fluorescent proteins (e.g., green fluorescent protein, red fluorescent protein, yellow fluorescent protein, blue fluorescent protein, cyan fluorescent protein, or variants thereof, including enhanced variants).

These genes can be incorporated into papilloma pseudoviruses using techniques well known to those of ordinary skill in the art. Suitable methods are described, for example, in Buck and Thomspon, Production of Papillomavirus-Based Gene Transfer Vectors. *Current Protocols in Cell Biology* 26.1.1-26.1.19, December 2007, which is hereby expressly incorporated by reference in its entirety.

Any reporter nucleic acid sequence may be used as a reporter gene if is it is detectable by a reporter assay. Reporter assays include any known method for detecting a nucleic acid sequence or its encoded protein product directly or indirectly. Reporter assays can be conducted in vitro or in vivo. For example, a reporter assay can measure the level of reporter gene expression or activity by measuring the level of reporter mRNA, the level of reporter protein, or the amount of reporter protein activity. The level of reporter mRNA may be measured, for example, using RT-PCR, ethidium bromide staining of a standard RNA gel, Northern blotting, primer extension, or nuclease protection assay. The level of reporter protein may be measured, for example, using chemiluminescence, microscopic analysis, Coomassie staining of an SDS-PAGE gel, Western blotting, dot blotting, slot blotting, ELISA, or RIA. Reporter protein activity may be measured using an assay specific to the reporter being used. For example, standard assays for luciferase, CAT, β-galactosidase, thymidine kinase (TK) assays (including full body scans; see Yu, Y. et al. (2000) Nature Medicine 6:933-937 and Blasberg, R. (2002) J. Cereb. Blood Flow Metab. 22:1157-1164), and fluorescent proteins are all well-known in the art. For instance, a Maestro (CRi, Woburn, Mass.) imaging device can be used to detect reporter gene expression.

Presence of the label can be detected in the subject using methods known in the art for in vivo scanning. These methods depend upon the type of label used. Skilled artisans are able to determine the appropriate method for detecting a particular label. Methods and devices that may be used in the diagnostic methods of the invention include, but are not limited to, computed tomography (CT), whole body scan such as position emission tomography (PET), single photon emission tomography (SPECT). magnetic resonance imaging (MRI), sonography, chemiluminescence, and the Maestro™ in-vivo imaging system (CRi, Inc.). In vivo scanning can be conducted in a local region of the subject (for example, the esophageal area can be scanned) or whole body scanning can be conducted.

Cancer cells expressing the genetic markers delivered by pseudoviruses can be identified as follows: for the HSV-tk gene, the subject can be administered radiolabeled 9-[(4[$^{18}$F] fluro-3-hydroxymethylbutyl)guanine (FHBG), administered intravenously, about 6000 μCi/Kg body weight of the recipient, (commercially available from PET Imaging Science Center, U. of South California). Expression of HSV-tk activity in cancer cells results in the accumulation of radiolabeled FHBG and can be monitored by Positron Emission Tomography (PET). In vivo GFP expressing cancer cells can be monitored by fluoresence microscopic examination of tissue sections. Tissue sections of Fluc or Rluc expressing cancer cells can be monitored by Cooled Charge-Coupled Device (CCD) cameras in vivo (commercially available from Xenogen Corp., Alamenda, Calif). $D_2R$ activity can be identified by administering 3-(2-[$^{18}$F]fluoroethyl)spiperone ([$^{18}$F] FESP) and monitored by PET. The following section describes examples of labels which can be chemically coupled to pseudoviruses or VLPs and examples of methods that can be used to chemically couple labels to pseudoviruses or VLPs.

Chemically Coupled Labels

Some embodiments also relate to methods of identifying cancers, tumors, metastases and pre-malignant conditions using papilloma pseudoviruses or VLPs labeled via chemical coupling. Chemically coupled labels include, but are not limited to, fluorescent dyes, phosphors, radionuclides, and other molecules known in the art that can be detected directly or indirectly.

Examples of fluorescent dyes include, but are not limited to, 7-Amino-actinomycin D, Acridine orange, Acridine yellow, Alexa Fluor dyes (Molecular Probes), Auramine O, Auramine-rhodamine stain, Benzanthrone, 9,10-Bis(phenylethynyl)anthracene, 5,12-Bis(phenylethynyl)naphthacene, CFDA-SE, CFSE, Calcein, Carboxyfluorescein, 1-Chloro-9,10-bis(phenylethynyl)anthracene, 2-Chloro-9,10-bis(phenylethynyl)anthracene, Coumarin, Cyanine, DAPI, Dark quencher, Dioc6, DyLight Fluor dyes (Thermo Fisher Scientific), Ethidium bromide, Fluorescein, Fura-2, Fura-2-acetoxymethyl ester, Green fluorescent protein and derivatives, Hilyte Fluor dyes (AnaSpec), Hoechst stain, Indian yellow, Luciferin, Perylene, Phycobilin, Phycoerythrin, Phycoerythrobilin, Propidium iodide, Pyranine, Rhodamine, RiboGreen, Rubrene, Ruthenium(II) tris(bathophenanthroline disulfonate), SYBR Green, Stilbene, Sulforhodamine 101, TSQ, Texas Red, Umbelliferone, or Yellow fluorescent protein.

Examples of phosphors include, but are not limited to Phosphor, Anthracene, Barium fluoride, Bismuth germanate, Cadmium sulfide, Cadmium tungstate, Gadolinium oxysulfide, Lanthanum bromide, Polyvinyl toluene, Scheelite, Sodium iodide, Stilbene, Strontium aluminate, Yttrium aluminium garnet, Zinc selenide, or Zinc sulfide.

Examples of suitable radioisotopic labels include, but are not limited to, $^{3}$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{211}$At, $^{212}$Pb, $^{47}$Sc, $^{109}$Pd, $^{186}$Re, $^{188}$Re, or $^{212}$Bi. Preferable radiolabeled pseudoviruses or VLPs are able to deliver more than 6000 rads to the tumor and have sufficient affinity so that the patient's bone marrow is not exposed to more than 300 rads. In some embodiments, 100, 1000, 1500, 2000, 2500, 3000, 3500, 4000, 4500, 5000, 5500, 6000, 6500, 7000, 7500, 8000, 8500, 9000, 9500, or 10000 rads to the cancer cells For example, $^{131}$I labeled coupled to the surface of pseudoviruses or VLPs is one example of a radiolabeled pseudoviruses or VLPs within the scope of these embodiments. Use of $^{131}$I labeled pseudoviruses or VLPs as well as other radiolabeled pseudoviruses or VLPs, is also within the scope of these embodiments. The pseudoviruses or VLPs can be radiolabeled, for example, by the Iodogen method according to established methods.

The detection may occur in vitro or in vivo. For example, fluorescent dyes (e.g., Alexa Fluor 488) can be coupled to the pseudoviruses by methods well known in the art (see, for example, Buck and Thomspon, Production of Papillomavirus-Based Gene Transfer Vectors. *Current Protocols in Cell Biology* 26.1.1-26.1.19, December 2007, which is hereby expressly incorporated by reference in its entirety).

In some embodiments, a radioactive imaging compound is chemically coupled to the pseudoviruses or VLPs. Radioactive chemical tracers which emit radiation such as gamma rays can be coupled to the pseudoviruses or VLPs to provide diagnostic information. In the case of yttrium oxide encasing layers, a positron emitter such as $^{87}$Y can be added to allow imaging. In the case of lanthanum phosphate, there are a variety of gamma emitters that may be used to add an imaging component to the treatment component.

A label may be chemically coupled directly to the pseudovirus or VLP (e.g., without a linking group) through an amino group, a sulfhydryl group, a hydroxyl group, or a carboxyl group.

In some embodiments, a label is attached to the pseudovirus or VLP via a linking group. The linking group can be any biocompatible linking group, where "biocompatible" indicates that the compound or group can be non-toxic and may be utilized in vitro or in vivo without causing injury, sickness, disease, or death. The label can be bonded to the linking group, for example, via an ether bond, an ester bond, a thiol bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoate (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

Chemically coupled labels can be detected using any of the methods described for detecting reporter genes. In one embodiment, the papilloma pseudovirus or VLP is labeled with a radioisotope and is detected in the patient using a radiation responsive surgical instrument (Thurston et al., U.S. Pat. No. 5,441,050). In another embodiment, the papilloma pseudovirus or VLP is labeled with a fluorescent compound and is detected in the patient using a fluorescence responsive scanning instrument. In another embodiment, the papilloma pseudovirus or VLP is labeled with a positron emitting metal and is detected in the patent using positron emission-tomography. In yet another embodiment, the papilloma pseudovirus or VLP is labeled with a paramagnetic label and is detected in a patient using magnetic resonance imaging (MRI). The following section provides greater detail on some embodiments that can be used to monitor cancer therapy.

Monitoring Cancer Therapy

The phrase "monitoring cancer therapy" refers to determining the relative amount of cancer cells in the body of a patient before, during and/or after anti-cancer therapy.

Some embodiments disclosed herein relate to methods for monitoring the progress or efficacy of cancer therapy in a subject. Subjects identified as having cancer and undergoing cancer therapy can be administered papillomavirus pseudovirus or VLP including labels as described above.

Subjects can be administered a papilloma pseudovirus or VLP that includes a label before the onset of treatment or during treatment. Cells containing the label can be assayed for and this measurement can be compared to one obtained at a subsequent time during the therapy and/or after therapy has been completed. In this way, it is possible to evaluate the inhibition of cancer cell proliferation, and the effectiveness of the therapy. Since only living cancer cells will contain the label, the therapy can continue until a minimal amount of label is detected.

Some embodiments disclosed herein also relate to methods for determining the amount of cancer cells present in a subject. By detecting the label, one can determine whether cancer cells are present within the subject and the amount of label measured is proportional to the amount of cancer cells present in the subject.

Diagnostic and Therapeutic Kits

Some embodiments include methods that utilize the pseudoviruses or VLPs in kits for the detection and/or treatment of tumors. The kits are based on the pseudovirus' or VLP's enhanced specificity towards cancer cells rather than a non-cancerous cells.

The diagnostic kits can comprise an effective amount of a labeled papilloma pseudovirus or VLP. The kits can further comprise an appropriate amount of non-cancerous control cells. The pseudovirus, VLP and/or cells may be supplied either frozen, lyophilized or growing on solid or in liquid medium. The diagnostic kits can further comprise inert ingredients and other kit components such as vials, applicators, packaging components and the like, which are known to those skilled in the art.

In an embodiment, a kit for the diagnostic detection of cervical cancer can be assembled. The kit can include a papilloma pseudovirus or VLP including a label (for example, a fluorescent label). The pseudovirus or VLP can be present in the kit in a liquid medium which can be aspirated onto the cervicovaginal mucosa of a subject. After an incubation period to allow the pseudovirus or VLP to selectively attach to suspected cancer cells, the cervicovaginal mucosa can be washed to remove excess unbound pseudovirus or VLP. Subsequently a detection device (for example, a fluorescent detection device) can be used to detect and/or measure the label included in the pseudovirus or VLP. The detection of label will indicate the presence of cancer cells.

Biomedical Applications

Embodiments disclosed herein also relate to methods of selectively inhibiting the proliferation of cancer cells (or pre-malignant cells) and/or killing cancer cells (or pre-malignant cells) without inhibiting proliferation of and/or killing normal cells. In some approaches, a subject that has cancer is identified using clinical or diagnostic techniques known in the art. The subject is then provided an inhibitory amount of papilloma pseudovirus or VLP that includes a therapeutic agent. Because the papilloma pseudovirus or VLP selectively attaches to cancer cells, a very focused and sensitive cancer therapy can be provided. In some embodiments, a pre-malignant condition can be treated using methods disclosed herein.

In some contexts, The phrase "selectively inhibiting" or "specific inhibition" indicates that the amount of normal cells that exhibit an inhibition of proliferation or are killed is less than or equal to 10%, 9%, 8%, 7%, 6%, 5%, 4%, 3%, 2%, 1%, 0.5%, 0.4, 0.3%, 0.2% 0.1%, 0.09%, 0.08%, 0.07%, 0.06%, 0.05%, 0.04%, 0.03%, 0.02%, 0.01%, 0.001%, 0.0001%, 0.00001%, or 0% of the total number of cells that have been contacted with the papilloma pseudovirus or VLP or at an inoculation site (e.g., a site of 1 $cm^2$, 1 $mm^2$, 1 $\mu m^2$, or 1 $nm^2$). A determination of specific inhibition, specific binding, or selective inhibition or selective binding of pseudoviruses or VLPs to cancer cells or pre-malignant cells can be determined by a range of methods known in the art or as described herein (e.g., competitive binding assays or Scatchard analyses). In some contexts, specific binding, specific inhibition, or selective binding or selective inhibition can be determined by mere observation, as shown in Example 11.

Therapeutic Genes

Therapeutic agents include, but are not limited to, therapeutic genes, proteins encoded by therapeutic genes, cytotoxins, and radionuclides. Therapeutic genes include, but are not limited to, tumor suppressor genes, pro-apoptotic genes, cytokines, enzymes, hormones, and immunomodulatory genes.

A "therapeutic gene" refers to a gene which can be administered to a subject for the purpose of treating or preventing a disease. For example, a therapeutic gene can be a gene administered to a subject for treatment of cancer. Examples of therapeutic genes include, but are not limited to, Rb, CFIR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11, IL-12, GM-CSF, G-CSF, thymidine kinase, mda7, fus, interferon alpha, interferon beta, interferon gamma, ADP, p53, ABL1, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

In certain embodiments, the therapeutic gene can be a tumor suppressor gene. A tumor suppressor gene refers to a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell.

Examples of tumor suppressor nucleic acids within this definition include, but are not limited to, APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEMA3 polypeptide and FUS1. Other exemplary tumor suppressor genes are described in publicly available databases of tumor suppressor genes. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied in the embodiments.

In certain embodiments, the therapeutic gene can be a gene that induces apoptosis (i.e., a pro-apoptotic gene). A "pro-apoptotic gene amino acid sequence" refers to a polypeptide that, when present in a cell, induces or promotes apoptosis. The present invention contemplates inclusion of any pro-apoptotic gene known to those of ordinary skill in the art. Exemplary pro-apoptotic genes include CD95, caspase-3, Bax, Bag-1, CRADD, TSSC3, bax, hid, Bak, MKP-7, PERP, bad, bcl-2, MST1, bbc3, Sax, BIK, BID, and mda7. One of ordinary skill in the art would be familiar with pro-apoptotic genes, and other such genes not specifically set forth herein that can be applied in the methods and compositions of the present invention.

The therapeutic gene can also be a gene encoding a cytokine. The term 'cytokine is a generic term for proteins released by one cell population which act on another cell as intercellular mediators. A "cytokine" refers to a polypeptide that, when present in a cell, maintains some or all of the function of a cytokine. This definition includes full-length as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines include, but are not limited to, lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10 IL-11, IL-12; IL-13, IL-14, IL-15, IL-16, IL-17, IL-18, IL-19, IL-20, IL-24 LIF, G-CSF, GM-CSF, M-CSF, EPO, kit-ligand or FLT-3.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-I antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, alpha-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, beta-endorphin, beta-melanocyte stimulating hormone, cholecystokinin, endothelin I, galanin, gastric inhibitory peptide, glucagon, insulin, lipotropins, neurophysins, somatostatin, calcitonin, calcitonin gene related peptide, beta-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

An "immunostimulatory nucleic acid or gene" as used herein is any nucleic acid containing an immunostimulatory motif or backbone that induces an immune response. The immune response may be characterized as, but is not limited to, a Th1-type immune response or a Th2-type immune response. Such immune responses are defined by cytokine and antibody production profiles which are elicited by the activated immune cells.

Examples of the immunomodulatory genes include chemokines, adhesive molecules, cytokines, co-stimulatory molecule, growth factors, and receptor molecules. The chemokines include MIP-1 alpha, MIP-1 beta, RANTEs, IL-8 and MCP-1. Examples of the adhesive molecules include selectin family constructs, mucin-like molecules, integrin family constructs, and immunoglobulin superfamily constructs. Examples of the select in family constructs include L-selectin, P-selectin, and E-selectin. The mucin-like molecules are ligands for the selectin family constructs. Examples of the mucin-like molecule include CD34, GlyCAM-1, and MadCAM-1. Examples of the integrin family constructs include LFA-1, VLA-1, Mac-1, and p150.95. Examples of the immunoglobulin superfamily constructs include PECAM-1, ICAMs (ICAM-1, ICAM-2, and ICAM-3), CD2, and LFA-3. Examples of the cytokine include mutants of M-CSF, GM-CSF, G-CSF, CSF, IL-4, and IL-18 (including deletion of the first about 35 amino acid residues which are present in the precursor of a protein but are not present in the protein in the mature form). Examples of co-stimulatory molecules include B71, B72, CD40 and CD40 ligands (CD40L). Examples of growth factors include IL-7, nerve growth factors, and a vascular endothelial growth factor. Examples of the receptor molecules include a Fas lethal gene expression product, a tumor necrosis factor TNF receptor, Flt, Apo-1, p55, WSL-1, DR3, TRAMP, Apo-3, AIR, LARD, NGRF, DR4, DR5, KILLER, TRAIL-R2, TRICK2, and DR6. The compositions of the present invention may contain caspase (ICE).

Therapeutic genes also include genes encoding polypeptides which are cytotoxic to cancer cells. Cytotoxic proteins include, but are not limited to, ricin, pokeweed toxin, diphtheria toxin A, saporin, gelonin, and Pseudomonas exotoxin A.

As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants. The nucleic acid molecule encoding a therapeutic gene may comprise a contiguous nucleic acid sequence of about 5 to about 12000 or more nucleotides, nucleosides, or base pairs.

Chemically Coupled Therapeutic Agents

Embodiments disclosed herein also relate to methods of inhibiting the proliferation of cancers, tumors, and metastases using papilloma pseudoviruses or VLPs chemically coupled to therapeutic agents. Chemically coupled therapeutic agents include, but are not limited to, therapeutic proteins as described above, cytotoxins, and radionuclides.

Cytotoxins include, but are not limited to, ricin, pokeweed toxin, diphtheria toxin A, saporin, gelonin, and Pseudomonas exotoxin A.

In an embodiment papilloma pseudoviruses or VLPs can be coupled to a radionuclide particle. The pseudovirus or VLP can attach to a binding site on the target cancer cells, and the radionuclide can administer a lethal dose of radiation. The basic strategy of radionuclide treatment is that coupling of a radionuclide to the pseudovirus or VLP causes enhanced accumulation of the radionuclide at the targeted site. Accumulation of the radionuclide at the targeted site causes radiation therapy to be delivered near the targeted site with a radius approximating the mean path length of the emitted particle.

Several different radionuclides can be considered for therapy. The choice of radionuclide takes into account the physical and chemical characteristics of the radionuclide, including half-life, radiation emission properties, radiolabeling properties, availability, in vivo distribution and stability. Suitable radionuclides possess a half-life long enough for target localization, little or no gamma radiation, intermediate beta particle energy, stable daughter products, and stable fixation with an antibody system. Many β-particle-emitting radionuclides are available. These include, for example, yttrium-90 ($^{90}$Y), iodine-131 ($^{131}$I), copper-67 ($^{67}$Cu) and rhenium-186 ($^{186}$Re). Alpha (α) particle-emitting radionuclides include astatine-211 ($^{211}$At), and bismuth-212 ($^{212}$Bi). Alpha and beta emitters are preferred because the mean path links are limited to dozens of mm, thereby limiting treatment to the immediate vicinity of the target. Beta particles may be more suitable for larger tumors due to the longer mean path length of the beta emission. Alpha particles generally have extremely high energies (greater than 5 MeV) and high linear energy transfer rates, which are useful for delivering high doses to a limited area.

Further embodiments disclosed herein relate to combinations of diagnostic and/or therapeutic methods described herein. For example, pseudoviruses can be constructed that comprise a therapeutic gene and a radionuclide. In other embodiments, pseudoviruses can be constructed that comprise Oligo T RNA and therapeutic gene.

Prodrugs

The term "prodrug" as used herein refers to a drug which is inactive as it is and becomes active when it is chemically changed in the body by a drug-metabolizing enzyme (e.g., purine and pyrimidine derivatives used as chemotherapeutic agents for cancer). Examples of the prodrugs herein preferably include ganciclovir, acyclovir, taxol, camptothecin, guanine nucleoside derivatives (e.g., A-5021), and the like. A prodrug herein preferable for the present invention is a prodrug which is converted to an active form by a suicide gene contained in a papilloma pseudovirus or VLP.

The term "suicide gene" as used herein refers to a gene which can kill the cell in which it is expressed. Representatively, such a gene is a metabolically toxic gene. For example, a method for introducing a suicide gene incorporated into a pseudovirus or VLP construct into cancer cells to drive them to suicide is herein exemplified. For example, thymidine kinase may be incorporated into a pseudovirus or VLP.

Oligo T RNA to Induce Tumor Regression

Anti-tumor therapeutic vaccines and anti-tumor cytotoxic gene therapy have produced limited clinical success, despite extensive effort. A simple approach that could combine the two activities might lead to more effective anti-tumor therapy. To accomplish this, a gene transfer vector that expresses oligo T RNA was constructed. In some embodiments, the RNA is expressed from a promoter, e.g. a Pol III promoter, as part of a papillomavirus pseudogenome after PsV transduction. This RNA will not be polyadenylated but will form a duplex with the poly A tails of cellular mRNAs. The double strand RNAs thus generated can lead to cytotoxicity by activation of PKR-mediated apoptosis and immunity through activation of TLR 3. The small size and dual function of this expression cassette leave open the possibility of expressing other genes in the up to 8 kb pseudogenome. Genes to increase immunogenicity, such as GMCSF, or cytotoxicity, such as TK, could be cotransduced by the oligo T PsV. Oligo T PsVs cannot be efficiently produced in most cells since the oligo T would be generated in the PsV producer cells and thus induce apoptosis prior to PsV assembly. However 293, and 293-derived lines, express adenovirus VA RNAs, which interact with PKR and prevent its activation by dsRNA. Oligo T PsV can be efficiently produced in a 293TT line. Other suitable cell lines include those that can express VA 1 RNAs and SV40 Large T-antigen such as 293FT cells (Invitrogen). The oligo T pseudogenome induced cytotoxicity after introduction into epithelial lines lacking VA RNAs. The Oligo T nucleic acid can be less than or equal to 200, 175, 150, 125, 100, 95, 80, 75, 70, 65, 60, 55, 50, 45, 40, 35, 30, 25, 20, 15, or 10 nucleotides.

Formulations

Embodiments disclosed herein also relate to methods of administering pseudoviruses or VLPs to a subject in order to contact cancer cells with pseudoviruses or VLPs. The routes of administration can vary with the location and nature of the tumor, and include, e.g., intravascular, intradermal, transdermal, parenteral, intravenous, intramuscular, intranasal, subcutaneous, regional, percutaneous, intratracheal, intraperitoneal, intraarterial, intravesical, intratumoral, inhalation, perfusion, lavage, direct injection, and oral administration and formulation.

The term "intravascular" is understood to refer to delivery into the vasculature of a patient, meaning into, within, or in a vessel or vessels of the patient. In certain embodiments, the administration can be into a vessel considered to be a vein (intravenous), while in others administration can be into a vessel considered to be an artery. Veins include, but are not limited to, the internal jugular vein, a peripheral vein, a coronary vein, a hepatic vein, the portal vein, great saphenous vein, the pulmonary vein, superior vena cava, inferior vena cava, a gastric vein, a splenic vein, inferior mesenteric vein, superior mesenteric vein, cephalic vein, and/or femoral vein. Arteries include, but are not limited to, coronary artery, pulmonary artery, brachial artery, internal carotid artery, aortic arch, femoral artery, peripheral artery, and/or ciliary artery. It is contemplated that delivery may be through or to an arteriole or capillary.

Injection into the tumor vasculature is specifically contemplated for discrete, solid, accessible tumors. Local, regional or systemic administration also may be appropriate. For tumors of greater than about 4 cm, the volume to be administered can be about 4-10 ml (preferably 10 ml), while for tumors of less than about 4 cm, a volume of about 1-3 ml can be used (preferably 3 ml). Multiple injections delivered as single dose comprise about 0.1 to about 0.5 ml volumes. The pseudoviruses or VLPs may advantageously be contacted by administering multiple injections to the tumor, spaced at approximately 1 cm intervals.

In the case of surgical intervention, pseudoviruses or VLPs can be administered preoperatively, to render an inoperable tumor subject to resection. Alternatively, pseudoviruses or VLPs can be administered at the time of surgery, and/or thereafter, to treat residual or metastatic disease. For example, a resected tumor bed may be injected or perfused with a formulation comprising pseudovirus or VLP that renders the pseudovirus or VLP advantageous for treatment of tumors. The perfusion may be continued post-resection, for example, by leaving a catheter implanted at the site of the surgery. Periodic post-surgical treatment can be carried out.

Continuous administration also may be applied where appropriate, for example, where a tumor is excised and the tumor bed is treated to eliminate residual, microscopic disease. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic pseudoviral constructs or VLPs may increase the resectability of the tumor due to shrinkage at the margins or by elimination of certain particularly invasive portions. Following treatments, resection may be possible. Additional treatments subsequent to resection can serve to eliminate microscopic residual disease at the tumor site.

A typical course of treatment, for a primary tumor or a post-excision tumor bed, can involve multiple doses. Typical primary tumor treatment can involve a 6 dose application over a two-week period. The two-week regimen may be repeated one, two, three, four, five, six or more times. During a course of treatment, the need to complete the planned dosings may be re-evaluated.

The treatments may include various "unit doses." Unit dose refers to a dose containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of pseudovirus and the titer attainable, one will deliver 1 to 100, 10 to 50, 100-1000, or up to about $10^4$, $10^5$, $10^6$, $10^7$, $10^8$, $10^9$, $10^{10}$, $10^{11}$, $10^{12}$, $10^{13}$, $10^{14}$, $10^{15}$ or higher infectious pseudoviral particles to the patient or to the patient's cells.

Injectable Compositions and Formulations

Injection of pseudoviruses or VLPs can be delivered by syringe or any other method used for injection of a solution, as long as the pseudovirus or VLP can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

The following examples provide illustrations of some of the embodiments described herein but are not intended to limit invention.

EXAMPLE 1

Genital Transmission of HPV in a Mouse Model is Potentiated by Nonoxynol-9 and Inhibited by Carrageenan A mouse model of cervicovaginal infection with HPV16 that recapitulates the establishment phase of papillomavirus infection was developed as follows.

Six- to eight-week-old female BALB/cAnNCr mice were obtained from the National Institutes of Health and housed and handled in accordance with their guidelines. Experimental protocols were approved by the National Cancer Institute's Animal Care and Use Committee. Unless otherwise noted, all mice received 3 mg of Depo-Provera (Pfizer) diluted in 100 µl of sterile PBS in a subcutaneous injection 4 d before pseudovirus challenge.

For vaginal challenge, mice designated for N-9 pretreatment received 50 µl of the N-9 containing compound intravaginally 6 h before intravaginal inoculation with pseudovirus. The material was delivered with an M50 positive-displacement pipette (Gilson), and standard dissecting forceps were used to occlude the vaginal introitus to achieve maximal retention of the material Mice designated for mechanical disruption underwent a procedure in conjunction with pseudovirus inoculation in which a Cytobrush cell collector (Cooper-Surgical) was inserted in the vagina and twirled clockwise and counterclockwise 10 times. The pseudovirus inoculum was a 20-µl dose composed of 5 µl of purified pseudovirus with a titer of $-5\times10^9$ IU/ml mixed with 15 µl of a 3% carboxymethylcellulose (CMC) preparation, with the exceptions of certain experiments in which 5 µl of inoculum was mixed with 5 µl of the indicated preparation, or in which 15 µl of inoculum was mixed with 5 µl of 4% CMC. In the N-9-pretreated mice, this dose was delivered as a one-time, atraumatic, intravaginal inoculation using an M20 positive-displacement pipette. In the Cytobrush-treated mice, the inoculum was delivered in two doses, 10 µl before and 10 µl after Cytobrush treatment, using an M20 positive-displacement pipette. Unless otherwise indicated, the reproductive tract was harvested on day 3 post-challenge after the mice were euthanized by $CO_2$ inhalation. For endocervical challenge, the endocervical canal was pretreated by direct instillation of 15 µl of 1% CMC or 15 µl of 1% CMC with 4% N-9. Six hours after pretreatment, 7 µl ($-1.4\times10^7$ IU) of pseudovirus mixed with 7 µl of 1% CMC was also deposited directly into the endocervical canal.

The results of these initial tests showed that the mouse model of cervicovaginal infection with HPV16 successfully recapitulated the establishment phase of papillomavirus infection. In the next example, the effects of nonoxynol-9 and carrageenan in the mouse model were evaluated.

EXAMPLE 2

Genital Transmission of HPV in a Mouse Model is Potentiated by Nonoxynol-9 and Inhibited by Carrageenan The ability of pseudoviruses to infect mechanically damaged cells, nonoxynol-9 treated cells, and carrageenan treated cells was investigated. The details of these experiments follows.

Gentle mechanical abrasion of the genital epithelium with a Cytobrush cell collector permitted detectable levels of pseudovirus infection. Whether chemical disruption of the genital epithelium could promote infection was also determined. N-9 is a nonionic, membrane-active surfactant that is widely used as a spermicide and is known to disrupt the normal architecture of animal and human genital epithelium. A formulation of 3% carboxymethylcellulose (CMC) designated to mimic the viscosity of a typical vaginal lubricant gel was made with or without 4% N-9. The gels were instilled in the vagina 6h before the mice were inoculated intravaginally with pseudovirus. The mice pretreated with CMC alone were not detectably infected, whereas those pretreated with either Cytobrush or with CMC and N-9 were highly susceptible to infection (P=0.05, 0.003, respectively) (FIG. 1a). Indeed, reporter signal intensity in the latter group was an average of fivefold stronger than infection-related signal induced by Cytobrush treatment (P=0.008). Conceptrol, an over-the-counter, CMC-based spermicide that contains 4% N-9, also sensitized the genital tract to pseudovirus infection to a greater degree than did Cytobrush treatment (P=0.02).

Figure 1C:
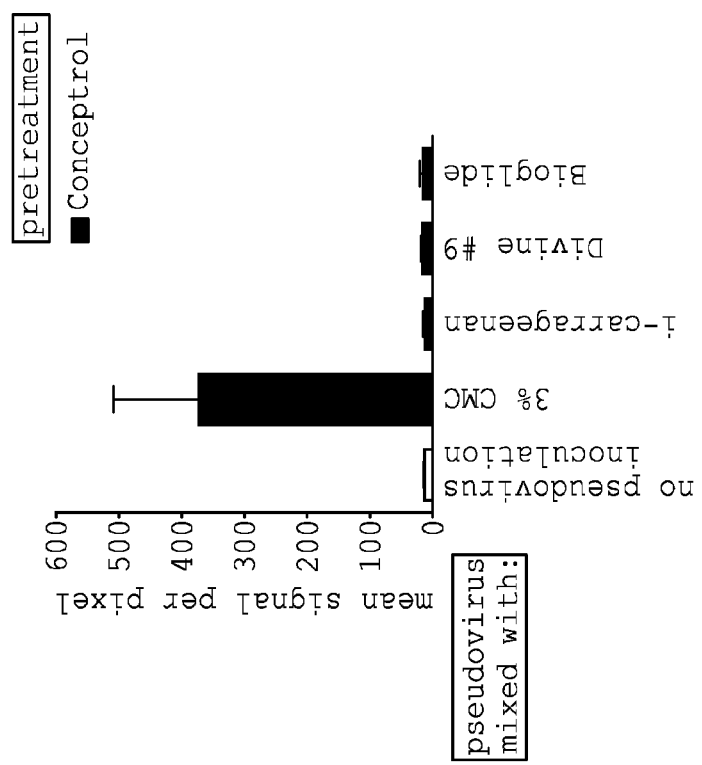

A wide range of genital HPV types can be potently inhibited in vitro by carrageenan, an inexpensive polysaccharide whose gelling properties have led to its incorporation into some over-the-counter vaginal lubricants. To test whether carrageenan can block infectivity in vivo, mice were challenged with HPV16 pseudoviruses premixed 1:1 with either 1% t-carrageenan or a 3% CMC preparation to control for the viscosity of the carrageenan preparation. Carrageenan prevented infection in the genital mucosa rendered susceptible to infection by either mechanical disruption (Cytobrush) or chemical disruption (N-9) (FIG. 1b). Two commercial carrageenan-containing lubricants (Divine No. 9 and BIOglide) that showed strong inhibitory activity in an in vitro pseudovirus assay similarly prevented detectable infection in vitro (FIG. 1c). To more closely mimic the conditions under which carrageenan might be used in common practice as a topical microbicide to prevent genital HPV transmission, N-9 in carrageenan or N-9 in control CMC gel was applied intravaginally 6 h before pseudovirus challenge. As expected, the CMC-based gel containing N-9 rendered the mucosa susceptible to significant HPV pseudovirus infection (P=0.03), while the carrageenan-based gel prevented detectable infection (FIG. 1d). When each of the carrageenan conditions were compared to the negative controls, P values were >0.1.

The experiments above demonstrate that mechanical disruption permits PsV infection, treatment with N-9 potentiates infection, and treatment with carrageenan inhibits infection. The example below demonstrates one method that can be used to couple a label to a pseudovirus.

EXAMPLE 3

Coupling of Alexa Fluor 488 Dye to Pseudovirions

Coupling of Alexa Fluor 488 dye to HPV16-RFP pseudovirions was performed according the manufacturer's instructions for protein labeling (A10235, Molecular Probes). The dye-coupled capsids were purified by gel filtration over a column of 2% 50- to 150-μm agarose beads (Agarose Bead Technologies). Re-titering of the dye-conjugated pseudovirion preparation confirmed that its infectivity remained comparable to that of nonlabeled pseudovirus.

The experiment above shows that labels can be successfully coupled to pseudoviruses and the infectivity of labeled pseudoviruses are comparable to that of nonlabeled pseudoviruses. The next example below demonstrates a technique for imaging labels coupled to or expressed in pseudoviruses.

EXAMPLE 4

Multispectral Fluorescence Imaging and Statistical Analysis

Figures 2A, 2B, 2C:
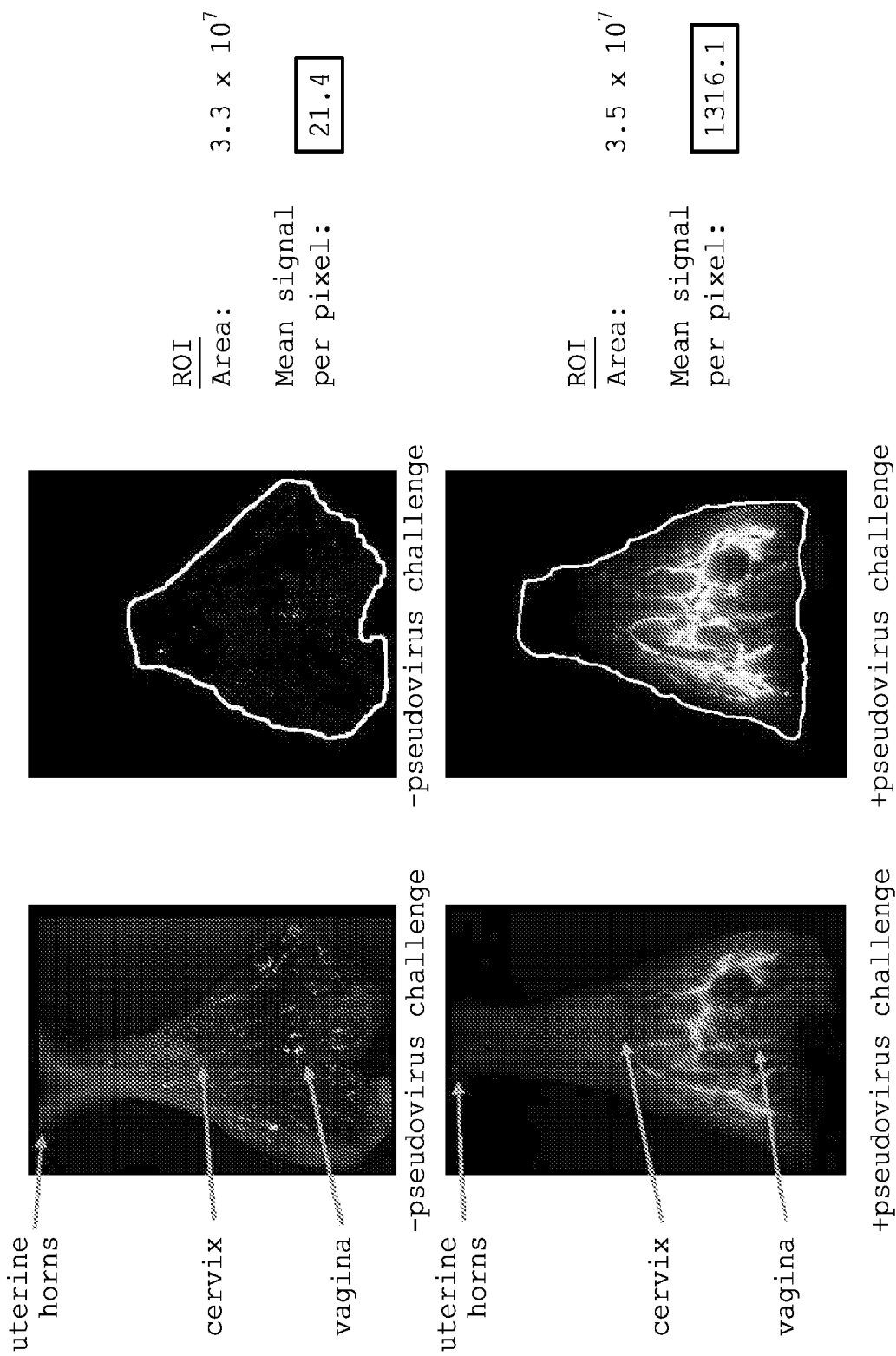
(FIG. 2a) Composite Maestro image (mucosal epithelium facing up) with unmixing algorithm applied. Red signal represents location of infection compared to background autofluorescence.
(FIG. 2b) Unmixed tdTomato signal converted to grayscale. Outline of tissue denotes ROI.
(FIG. 2c) ImageJ analysis. Mean signal per pixel within the ROI was computed.

To generate a more quantitative assay for cervicovaginal infection, a method for measuring the total reporter gene expression in whole tissue samples using a multispectral fluorescence imaging device was developed. For these analyses, the entire mouse vagina and cervix were assessed for reporter gene expression, which generated data on the distribution and intensity of infection and the mean intensity per pixel, thus allowing quantitative comparison between specimens (FIG. 2).

The reproductive tract of each mouse, from the external genitalia to the lower half of the uterine horns, was excised and stored in PBS on ice for <6 h before imaging. A Maestro (CRi, Woburn, Mass.) imaging device with a green excitation filter and a 580-nm long-pass emission filter was used to obtain images from 550 nm to 9.00 nm in 10-nm wavelength increments. Using the spectral signature of RFP in infected tissues as signal and the background autofluorescence in uninfected tissues as noise, a spectral unmixing algorithm was applied to the composite images to determine the intensity and location of infection. The open-source software Image J, available online, was used to calculate the mean signal per pixel in a region of interest (ROI) in the grayscale representation of unmixed signal. The mean of the numbers thus generated represents the result of each particular experimental condition. In some cases, to determine whether the difference between these means was statistically significant, an unpaired Student's t-test was performed and the results reported in the text as a P value.

Conceptrol-treated mice were mock infected or challenged with HPV-16-tdTomato pseudovirus. After 3 days, the entire reproductive tract was dissected out and the ventral wall of the vagina and cervix incised sagitally. Composite Maestro image with unmixing algorithm was applied. Red signal represented the location of infection compared to background autofluorescence. Unmixed tdTomato signal was converted to grayscale. ImageJ analysis. Mean signal per pixel within the ROI was computed. For mock treated mice, the ROI Area was $3.3 \times 10^7$ and the mean signal per pixel was 21.4. For pseudovirus-challenged mice, the ROI Area was $3.5 \times 10^7$ and the mean signal per pixel was 1316.1.

EXAMPLE 5

The Intact Cervicovaginal Mucosa is Resistant to HPV Infection (Methods of N-9/Carrageenan Example)

Figure 3:
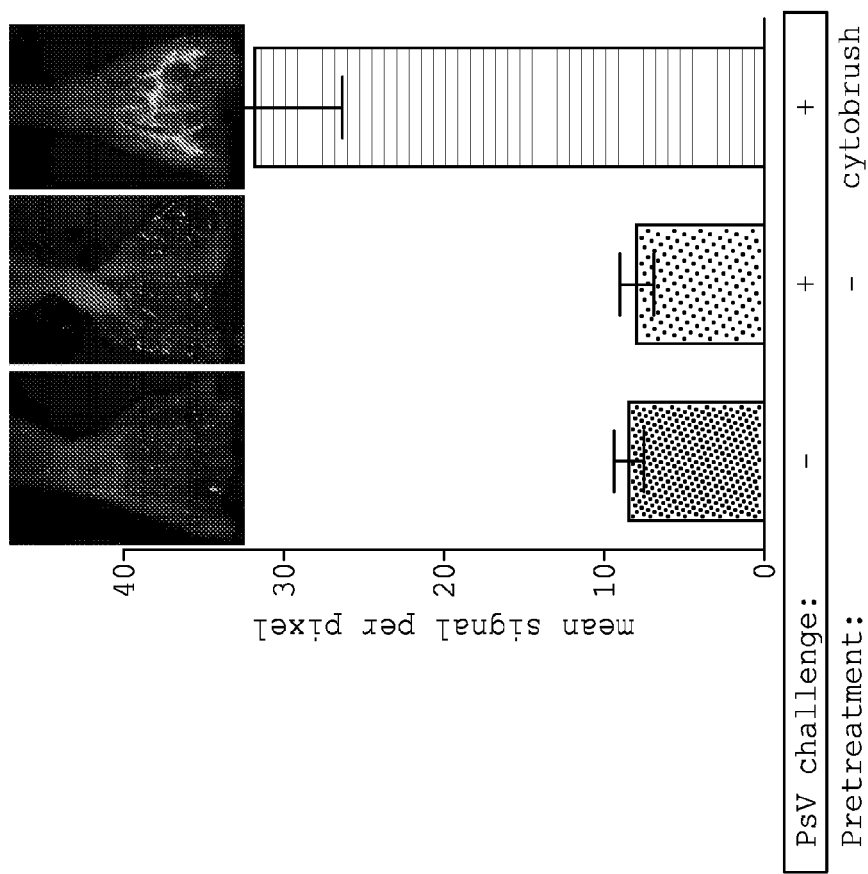
FIG. 3. The mouse intact genital tract was completely resistant to infection after deposition of $10^7$ pseudoviral infectious units into the vagina or endocervical canal.

Red Fluorescent Protein (RFP) PsV was used to study papillomavirus infection of the mouse genital tract. Surprisingly, it was found that the intact genital tract was completely resistant to infection after deposition of $10^7$ infectious units into the vagina or endocervical canal. (FIG. 3) Even more surprising, green fluorescent dye-coupled virus bound neither the squamous or simple epithelium that lines the female reproductive tract. (FIG. 4)

EXAMPLE 6

HPV Pseudoviruses Do Not Infect Intact Normal Tissue

HPV16 pseudovirions containing the RFP expressing plasmid (approximately $10^8$ tissue culture infectious units) was administered atraumatically onto the following tissue surfaces: oropharygeal mucosa, tongue, small intestines, large intestine, anal canal, eye conjunctiva, trachea, bronchi, parietal peritoneum, gastrointestinal tract serosa, gastrointestinal tract mesentery, liver, spleen, bladder, uterus, ovaries, external skin and lung parenchyma. Infection, as assessed by red fluorescence using confocal microscopy, was only observed in the lung parenchyma. The following example demonstrates that pseudoviruses selectively infect cancer cell lines.

EXAMPLE 7

HPV Pseudoviruses Infect Many Human Tumor-Derived Cell Lines

Figure 5:
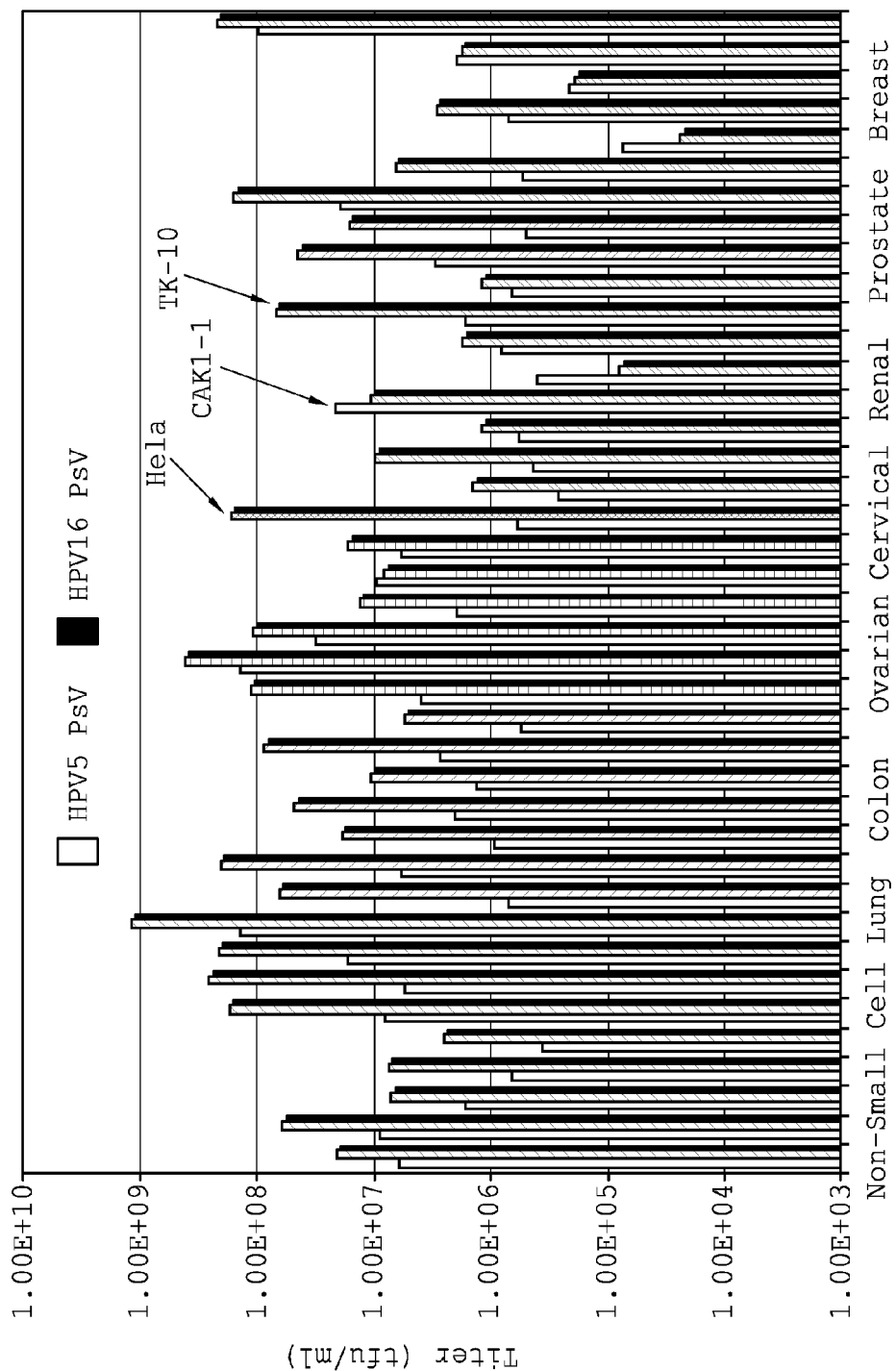
FIG. 5. Epithelial tumor cell lines were permissive for HPV5 and 16 pseudovirus infection.
Figure 6:
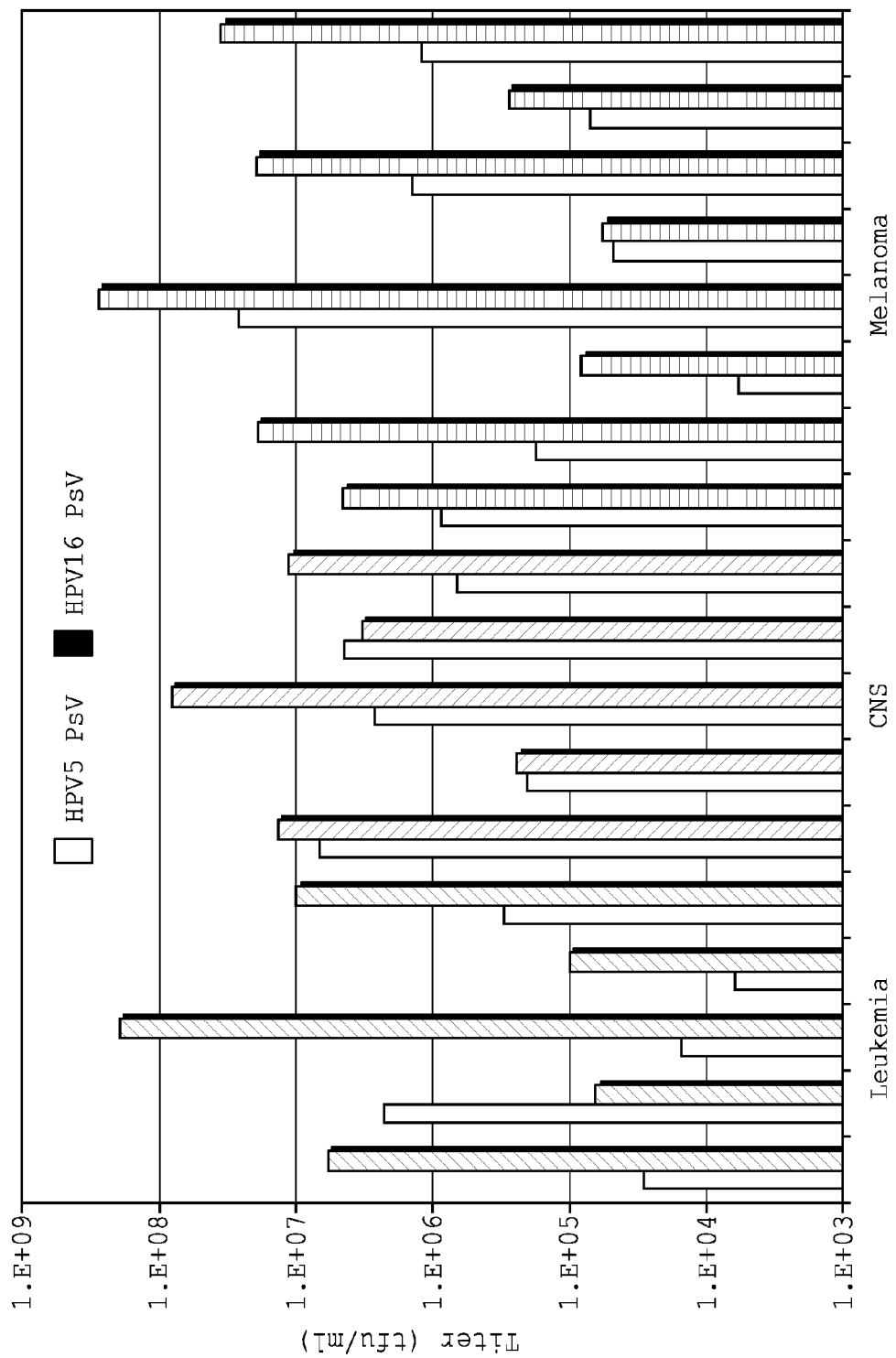
FIG. 6. Non-epithelial tumor cell lines were permissive for HPV5 and 16 pseudovirus infection.

A panel of 59 human tumor cell lines was obtained from the National Cancer Institute's Developmental Therapeutics Program (DTP) In Vitro Cell Line Screening Project (IVCLSP), for the purpose of testing infectability by HPV pseudoviruses (FIGS. 5 and 6). HPV5 and HPV16 pseudovirions were chosen for the screen as representative of cutaneous and mucosatropic HPVs, respectively. The purified infectious pseudoviruses containing GFP reporter plasmids were prepared as described in Buck, C. B., Pastrana, D. V., Lowy, D. R., Schiller J. T. Generation of HPV pseudovirions using transfection and their use in neutralization assays. Methods Mol. Med. 119:445-462, 2005, which is hereby expressly incorporated by reference in its entirety. For HPV5, plasmids p5L1w, p5L2w and pfwb were used; and or HPV16, p16shell and pfwb plasmids were used. Purified pseudoviruses were titered on 293TT cells as described in Buck et al. above, and titer of stocks determined to be $1.4 \times 10E9$ infectious units/ml for HPV16 and $2.2 \times 10E7$ infectious units/ml for HPV5.

The 59 human tumor cell lines from the DTP were inoculated into 96 well flat-bottomed microtiter plates in 100 µL at plating densities ranging from 5,000 to 40,000 cells/well depending on the doubling time of individual cell lines.

In addition, HeLa, a human cervical epithelial cell line, (catalog # CCL-2, ATCC, Manassas, Va. 20108) was inoculated the same way as the tumor cell lines at 5,000 cells/well. All cell lines were grown in RPMI 1640 medium containing 5% fetal bovine serum and 2 mM L-glutamine. After cell inoculation, the microtiter plates were incubated at 37° C., 5% CO2, 95% air and 100% relative humidity for 24 hours prior to addition of pseudovirus. Three, ten-fold serial dilutions were made of each pseudovirus in DPBS+0.8M NaCl. Five µl of each dilution, undiluted pseudovirus and DPBS+0.8M NaCl (background) were added into duplicate wells for each cell line. Plates were incubated at 37° C., 5% CO2, 95% air and 100% relative humidity for 24 hours prior to addition of 150 µl/well RPMI 1640 medium containing 5% fetal bovine serum and 2 mM L-glutamine. Plates were incubated for another 48 hours prior to FACS analysis (72 hour total infection time). The cells from each well were harvested separately and subject to FACS analysis. The percent of GFP positive cells was determined for each sample. Values obtained from duplicate samples were averaged and the background was subtracted. The dilution of pseudovirus that produced 1-10% GFP positive cells (in the linear range of the FACS analysis) was used to calculate the HPV5 and HPV16 virus titers. As shown in FIGS. 5 and 6, the panel of tumor cell lines were permissive for HPV5 and 16 pseudovirus infection. The experiments above indicate that papilloma pseudoviruses specifcally infect cancer cell lines. The next example demonstrates that pseudoviruses selectively infect tumor cells in vivo.

EXAMPLE 8

Figure 7:
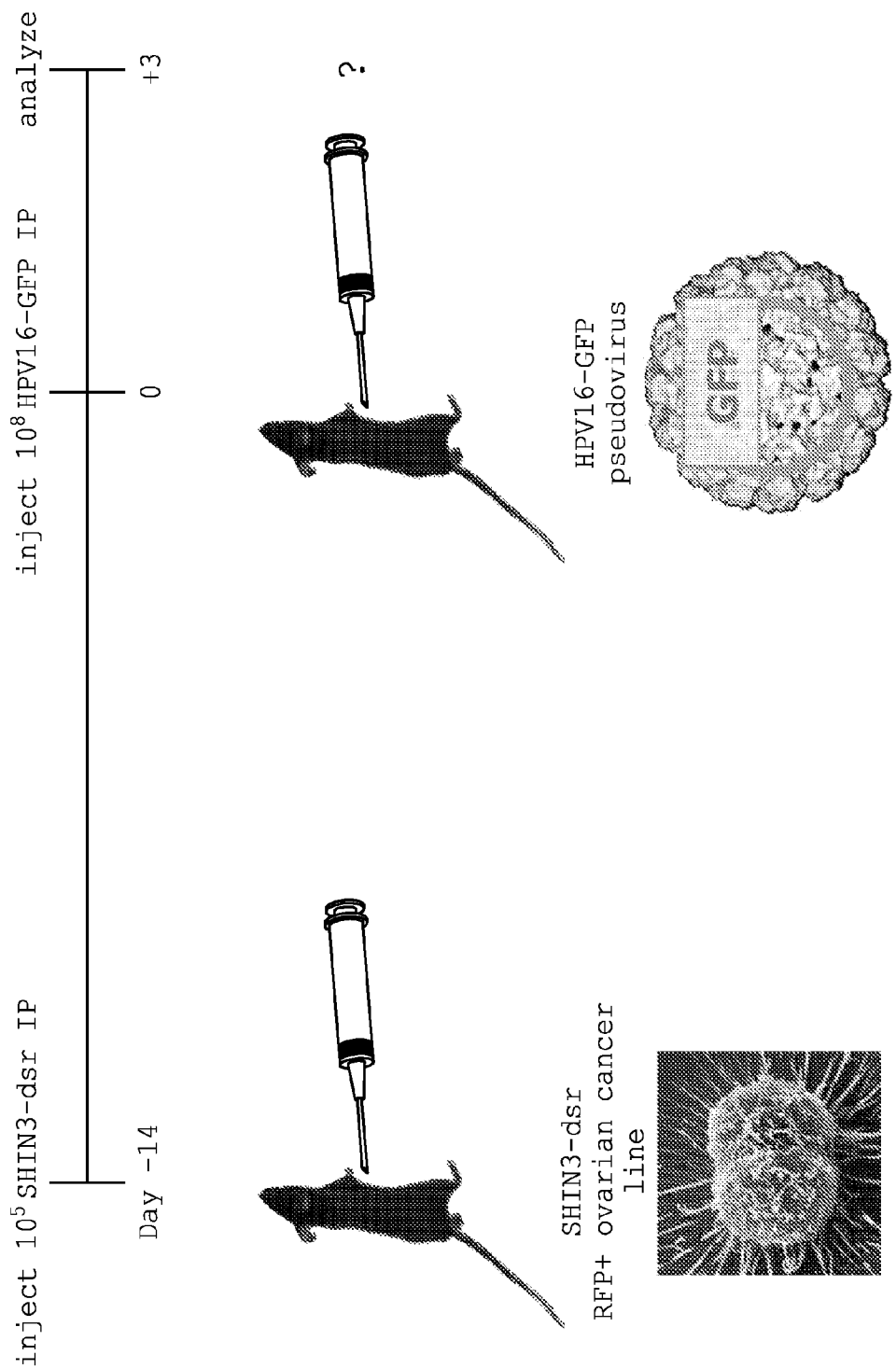
FIG. 7. Experimental design to test whether papilloma pseudoviruses preferentially infect tumor cells in a SHIN3-dsr peritoneal tumor metastisis model.
Figure 8:
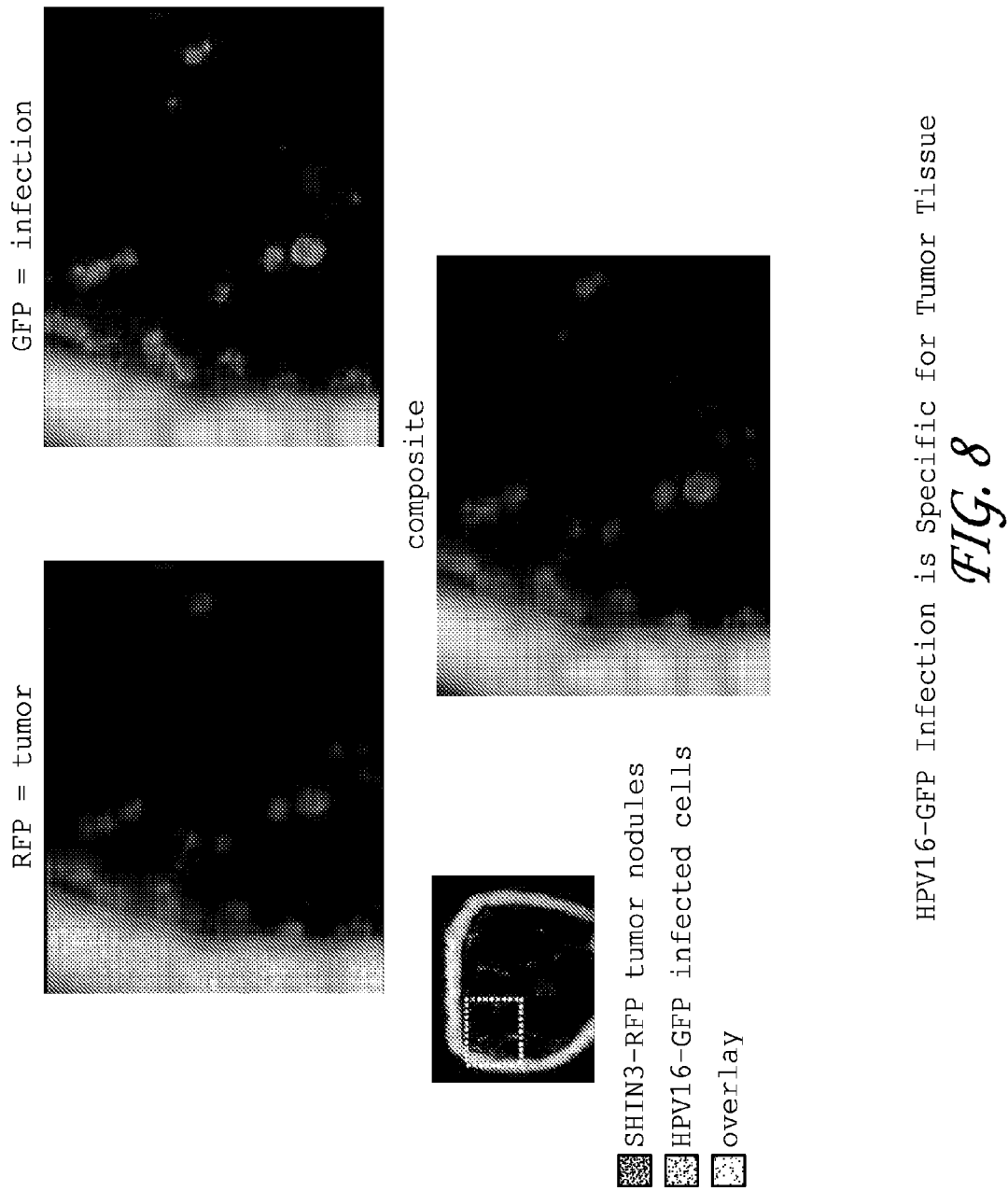
FIG. 8. HPV16 pseudovirus efficiently and selectively infects ovarian cancer cells implanted on the peritoneal membrane as demonstrated by multispectral fluorescence imaging.

HPV Pseudoviruses Preferentially Infect Tumor Cells in a Peritoneal Tumor Metastasis Model An established murine ovarian cancer tumor model was used to test the efficiency and specificity of pseudovirus infection of peritoneal tumor nodule implants. This model uses SHIN3-DSR[1], which is a human ovarian cancer cell line stably transfected with a red fluorescent protein (RFP) plasmid so that RFP is constructively expressed in the tumor cell (FIG. 7). Intraperitoneal tumor xenografts were established in female nude mice 14 days after i.p. injection of $2 \times 10^6$ SHIN3-DSR's in 200 ul of sterile PBS. Three days after i.p. injection of $5 \times 10^9$ infectious units (IU) of HPV16-GFP in 300 ul of sterile PBS, the mice were euthanized and the peritoneal membranes were analyzed by multispectral fluorescence imaging. The anatomy of the imaged tissue and the conceptual framework for the imaging are similar to that found in Reference 1, FIG. 4c. Specifically, a portion of the peritoneal membrane of the gut mesentery was selected at random and spread out on a nonfluorescent plate. Two separate composite images were obtained with a Maestro imaging device. For the first, a band-pass filter from 445 to 490 nm and a long-pass filter over 515 nm were used for emission and excitation light, respectively. The tunable filter in the Maestro was automatically stepped up in 10-nm increments from 500 to 800 nm while the camera captured images at each wavelength interval with a constant exposure. For the second, the band pass and longpass filter were 503 to 555 and 580, respectively, and the 10nm wavelength increments ranged from 500 to 800. A spectral unmixing algorithm was applied to the first image to obtain an unmixed image of GFP and of autofluorescence. A separate algorithm was applied to the second image to obtain an umixed image of RFP and of autofluorescence. These two final images are displayed, along with the overlay, demonstrating a high degree of colocalization of signal. Following multispectral imaging, these tissues were snap frozen, sectioned on a cryotome and analyzed by confocal microscopy. This confirmed HPV16-GFP infection by demonstration of GFP expression in RFP-expressing SHIN3-DSR tumor nodules. In addition, confocal analysis showed minimal, if any, pseudovirus infection of adjacent normal peritoneal membrane. This experiment indicated that HPV16 pseudovirus efficiently infected ovarian cancer cells implanted on the peritoneal membrane (FIG. 8). It further showed that infection was highly specific for tumor cells, with normal peritoneal surfaces spared from infection.

Figure 9:
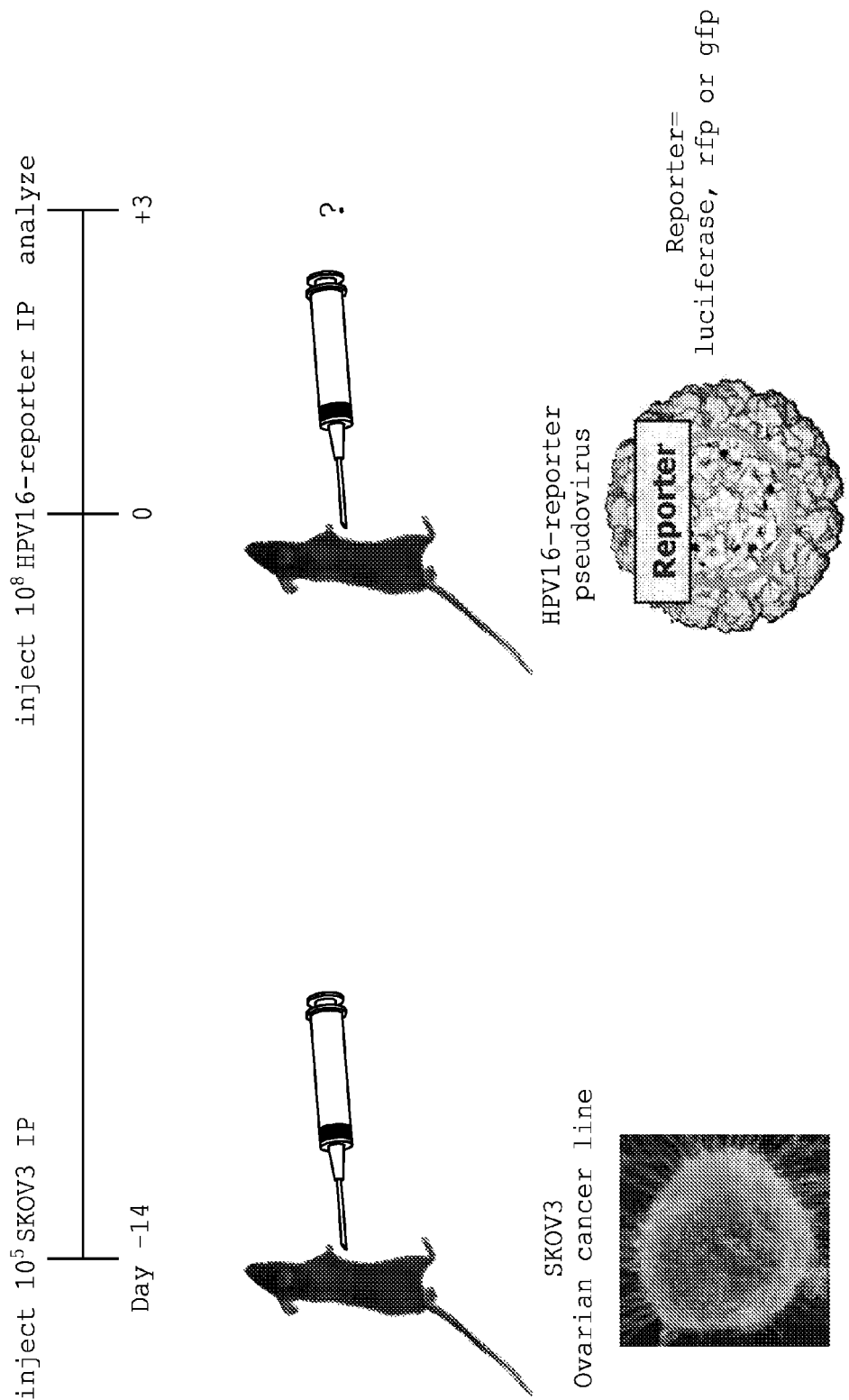
FIG. 9. Experimental design to test whether papilloma pseudoviruses preferentially infect tumor cells in a SKOV3 peritoneal tumor metastisis model.

Similar results were obtained in a murine model that used SKOV3, a human ovarian cancer cell line, were injected (FIG. 9). Just as above, Intraperitoneal tumor xenografts were established in female nude mice 14 days after i.p. injection of $1 \times 10^5$ SKOV3 cells. Three days after i.p. injection of $1 \times 10^8$ infectious units (IU) of HPV16 PsV-luciferase or HPV16 PsV-RFP, the mice were euthanized and the peritoneal membranes were analyzed by multispectral fluorescence imaging as discussed above.

HPV16-Luciferase

Figure 10:
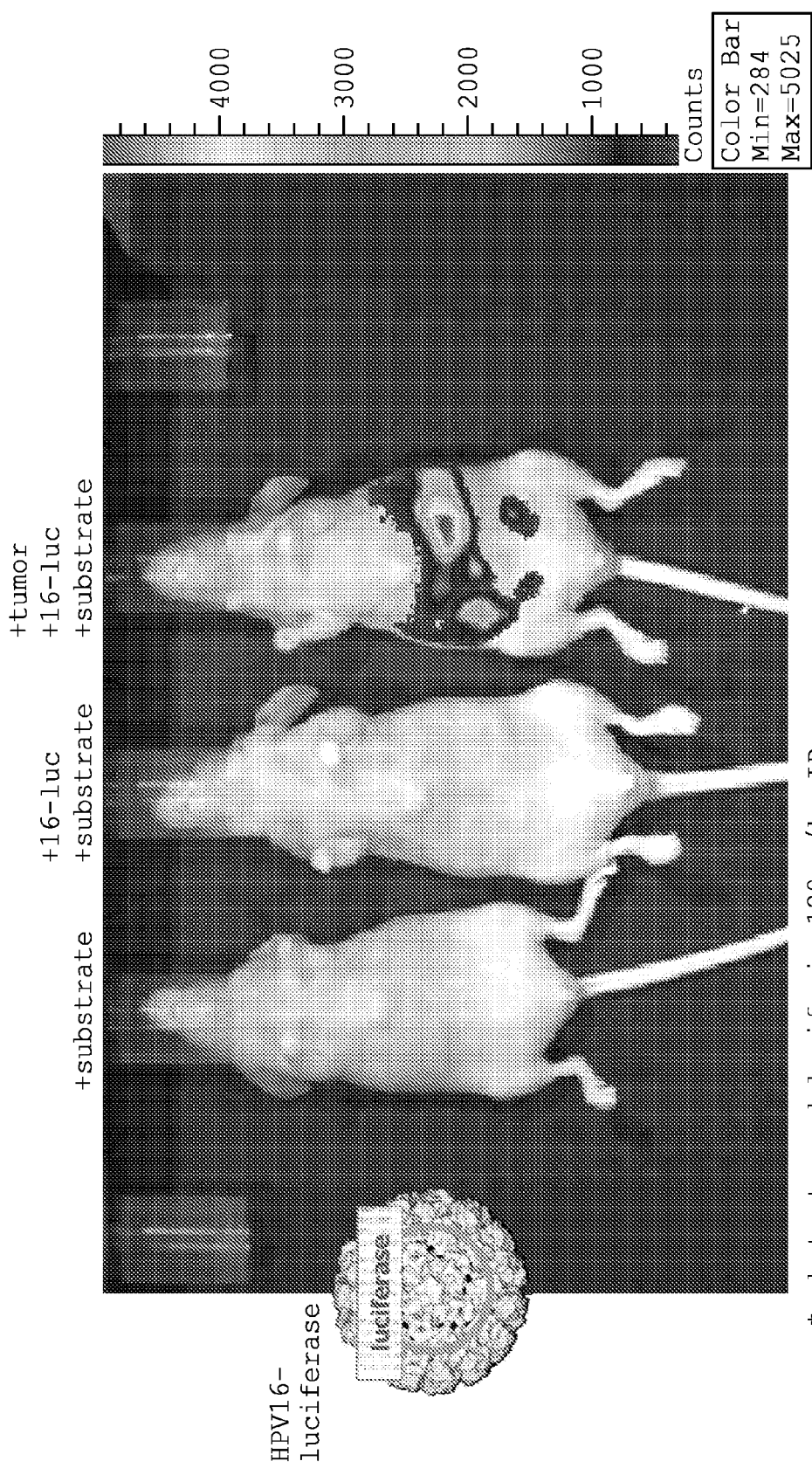
FIG. 10. HPV16 pseudovirus efficiently and selectively infects ovarian cancer cells implanted on the peritoneal membrane as demonstrated by measuring luciferase activity.

No signal was observed in control mice that lacked both HPV16 PsV-luciferase and tumors, but where substrate (d-luciferin 120 mg/kg i.p.) was added. In addition, no signal was observed in control mice that lacked tumors, but received HPV16-luciferase and substrate. In mice that possessed tumors, HPV16-luciferase, and substrate, a significant signal was observed. (FIG. 10)

HPV16-RFP

Figure 11:
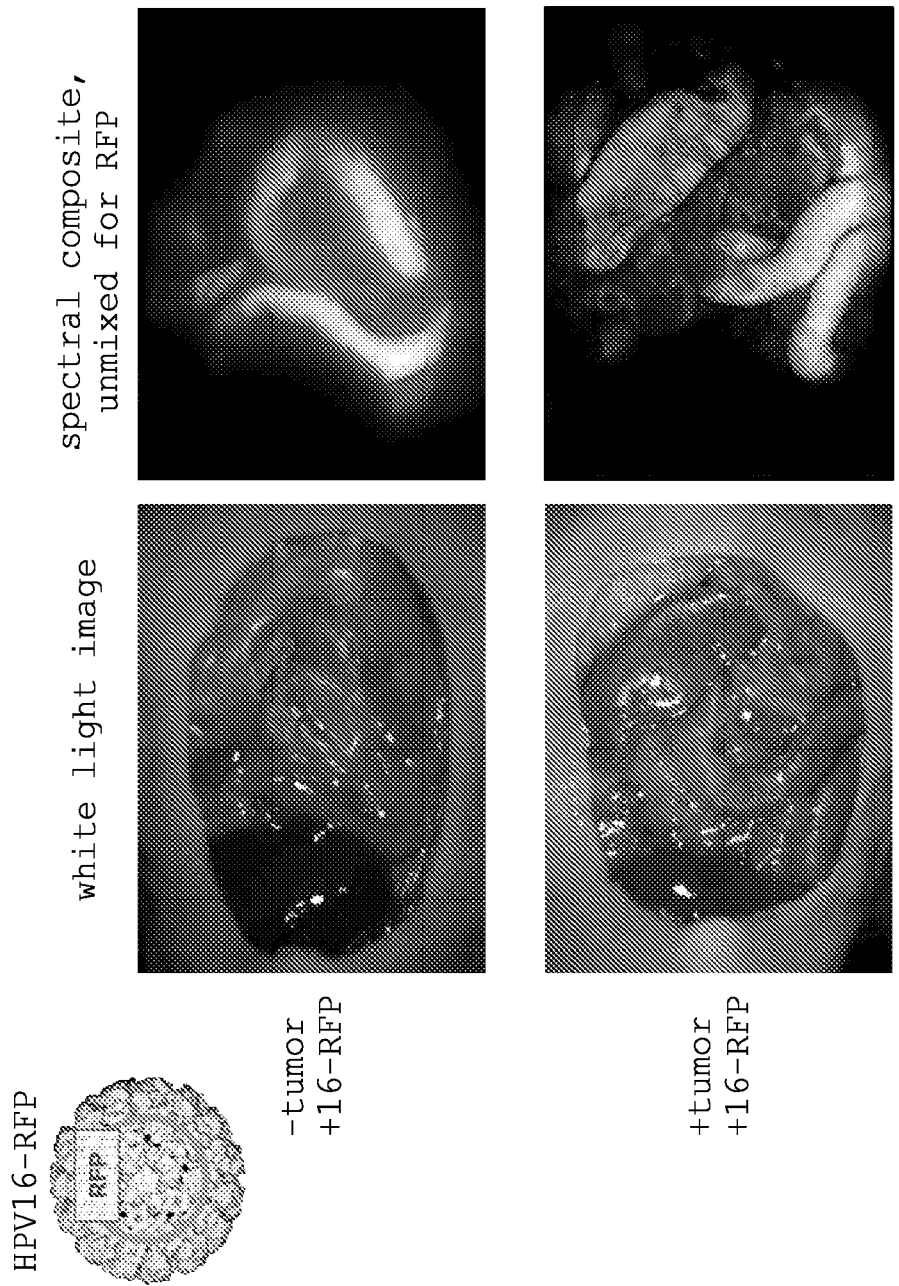
FIG. 11. HPV16 pseudovirus efficiently and selectively infects ovarian cancer cells implanted on the peritoneal membrane as demonstrated by multispectral fluorescence imaging.

No signal was observed in control mice that were injected with HPV16 PsV-RFP but lacked tumors. In mice that possessed tumors and received HPV16 PsV-RFP, significant fluorescence was observed. (FIGS. 11 and 12).

These experiments confirmed the finding that HPV16 pseudovirus efficiently infected ovarian cancer cells implanted on the peritoneal membrane. It further confirmed that infection was highly specific for tumor cells, with normal peritoneal surfaces spared from infection.

EXAMPLE 9

HPV Pseudovirus-Mediated Suicide Gene Therapy of Ovarian Carcinoma

Based on NCI-60 human tumor-derived cell line survey, and on the results of the experiment described above, it is contemplated that intraperitoneal delivery of pseudovirus will result in efficient and specific infection of ovarian cancer cells confined to the peritoneal cavity, and that this method can be used to treat ovarian cancers. By one approach a method of suicide gene therapy, in which transduction of the gene for herpes simplex thymidine kinase (TK) is followed by systemic treatment with the prodrug, gangcyclovir. In both the SHIN3 nude mouse model, and in the MOSEC syngeneic, immunocompetent mouse model for ovarian cancer, it is contemplated that xenografted intraperitoneal tumor cells will be efficiently transduced by HPV16-TK pseudovirus, and that TK-expressing tumor cells will convert systemically administered gangcyclovir to its toxic triphosphate metabolite, killing tumor cells. This will result in a therapeutic response, as measured by decreased tumor burden and increased survival time in xenografted mice. Alternatively pseudovirus expressing the oligo T will be used to induce regression of the tumor cells. Furthermore, based on the NCI-60 cell line experiments, it is contemplated that fresh explants of human ovarian carcinomas will be permissive to pseudovirus infection. This phenomenon is illustrated using a protocol similar to one previously described[2], in which the Krumdieck thin-slice tissue culture system is used to prepare thin sections of cancer nodules suitable for analysis of virus transduction ex vivo. (See e.g., 1. Hama, Y. et al. A target cell-specific activatable fluorescence probe for in vivo molecular imaging of cancer based on a self-quenched avidin-rhodamine conjugate. *Cancer Res* 67, 2791-9 (2007) and 2. Kirby, T. O. et al. A novel ex vivo model system for evaluation of conditionally replicative adenoviruses therapeutic efficacy and toxicity. *Clin Cancer Res* 10, 8697-703 (2004)).

EXAMPLE 10

Oligo T Expressing HPV Psuedoviruses for Combined Cytotoxicity and Immunity to Tumors Oligo T expressing pseudoviruses were prepared in order to provide a simple approach to combine anti-tumor therapeutic vaccines and anti-tumor cytotoxic gene therapy.

Construction of pPolyT plasmid:

```
Two oligos
(GCGGCGTCTAGAATTTTTTTTTTTTTTTTTTTTTTTTTTTTTTTT
TTTTTTTTTT; SEQ ID NO: 1)
and

GCGGCGTCTAGAAAAAAAAAAAAAAAAAAAAAAAAAAAAAAAAAAAAAAA
AAAAAAAAA; SEQ ID NO: 2)
``` were snap-annealed, then extended with T4 DNA polymerase (New England Biolabs). The resulting duplexed DNA was digested with Xba I and ligated into the Xba I site of a murine pol-1 promoter/terminator construct, p417-Ron (obtained from Ron A. M. Fouchier, Erasmus Medical Center, the Netherlands). Clones were sequenced, and a clone with a 45 basepair T tract on the sense strand was selected.

Experiment Documentation of pPolyT Cytotoxicity:

HaCaT cells were transfected with pBluescript II KS+ (Stratagene) or pPolyT using Lipofectamine LTX (Invitrogen). 48 hours later, the cells were inspected by light microscope and treated with a colorimetric metabolic substrate (WST-1, Roche). Cells receiving pPolyT exhibited reticulated morphology and were quite sparse relative to pBluescript transfected (or untransfected) cells. Turnover of WST-1 was reduced by >2-fold in the pPolyT transfected cells.

EXAMPLE 11

Intravenous Administration of HPV Pseudovirus Targets Lung Metastases

Figure 13:
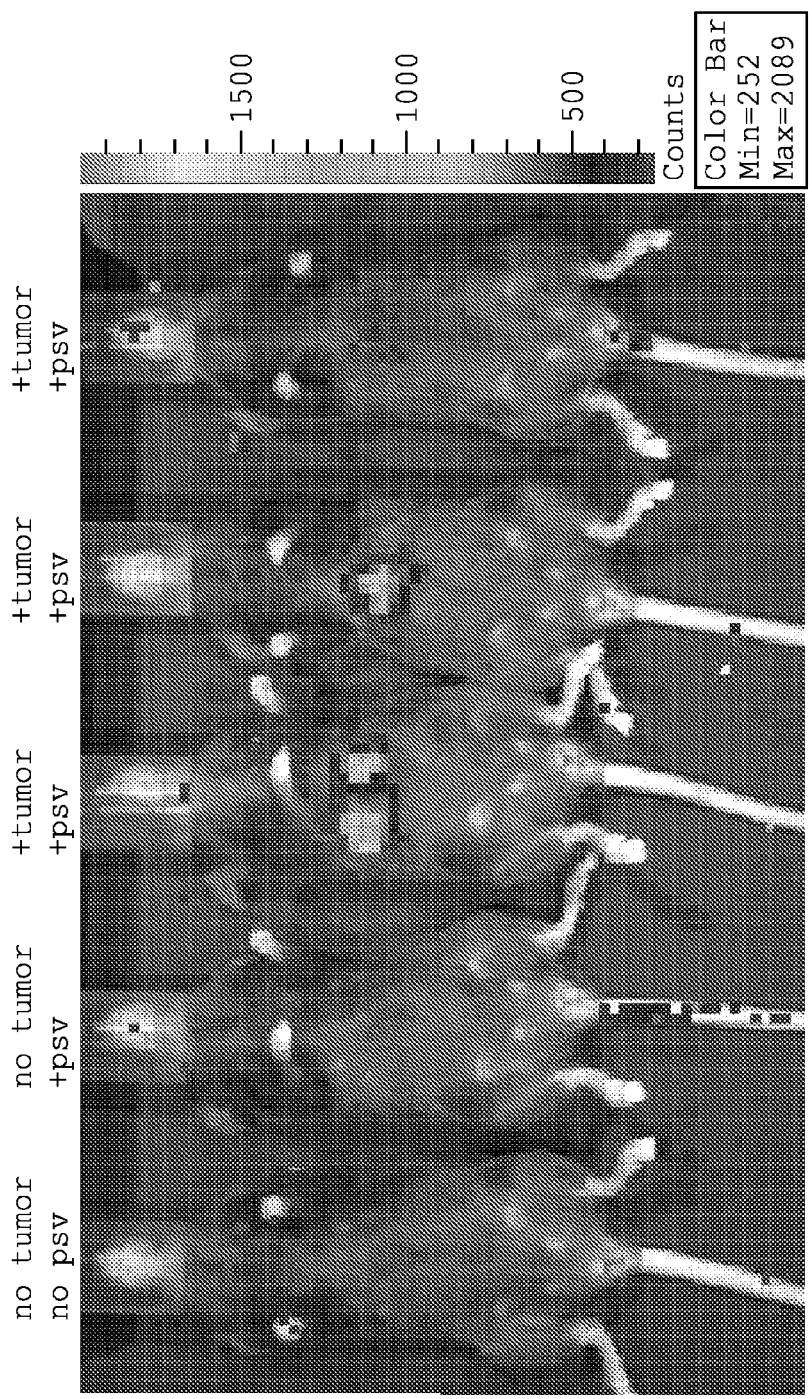
FIG. 13. HPV16 pseudovirus efficiently and selectively infects lung metastases as demonstrated by multispectral fluorescence imaging.

According to an established protocol for producing lung tumor metastases (see, e.g., Qian et al. Prophylactic, therapeutic and anti-metastatic effects of an HPV-16 mE6Δ/mE7/TBhsp70Δ fusion protein vaccine in an animal model. Immunology Letters 102(2):191-201 (2006)), a series of mice were injected with 2×104 TC-1 cells intravenously 2 weeks prior to the experiment. All mice were then treated with approximately 1×107 HPV16 PsV-luciferase intravenously, including the control animals, which received saline instead of tumor cells. Luciferase activity was subsequently measured upon introduction of substrate. No signal was detected in the control mice. In the mice that had been inoculated with tumor cells, significant signal was detected, indicating the pseudoviruses efficiently targeted lung metastases (FIG. 13). This experiment demonstrated that intravenous administration of pseudovirus results in specific targeting of tumor cells and sparing of normal tissue, similar to the pattern demonstrated after administration by other routes.

EXAMPLE 12

Diagnosis and Treatment of Cervical Cancer

A subject having cervical cancer is provided a composition comprising a papilloma VLP coupled to a radionuclide (e.g., $^{3}$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{211}$At, $^{212}$Pb, $^{47}$Sc, $^{109}$Pd, $^{186}$Re, $^{188}$Re, or $^{212}$Bi). The composition can be provided in an amount of approximately 0.1 mg to approximately 10 mg. Alternatively, the composition can be provided in an amount sufficient to deliver 100, 1000, 1500, 2000, 2500, 3000, 3500, 4000, 4500, 5000, 5500, 6000, 6500, 7000, 7500, 8000, 8500, 9000, 9500, or 10000 rads to the cancer cells. The composition can be provided in a convenient vaginal application and the composition may be in a liquid or gel form. The composition comprising the papilloma VLP coupled to the radionuclide is provided to the subject and the labeled VLPs are allowed to bind to the cervical cancer cells for 2, 4, 6, or 8 hours. After binding, the unbound labeled VLPs are removed by successive lavage. The amount of radioactivity present in the vaginal canal is assessed by dosimetry determinations (e.g., dosimetry badges). A new badge is provided daily for 4 weeks and the badges are collected at the end of the evaluation and a gradual decrease in radioactive exposure will be seen over time.

It is also envisioned that a weekly cervical biopsy will be taken so as to evaluate the histological reduction of cancer cells during the experiment. The results will show that the radiolabeled VLPs selectively bound and identified the cervical cancer cells in the subject's vaginal canal and, overtime, the radioactivity contributed to the reduction of the presence and proliferation of the cancer cells and the restoration of normal cell morphology, as compared to untreated control subjects.

What is claimed is:

1. A method of inhibiting the proliferation of cancer cells and/or killing cancer cells comprising
administering to a subject having cancer a composition that comprises a therapeutic agent formulated with a papilloma pseudovirus or a papilloma VLP, wherein the therapeutic agent is selected from the group consisting of:
a) a gene selected from the group consisting of:
  i) a tumor suppressor gene;
  ii) a pro-apototic gene;
  iii) a gene encoding a cytokine, a lymphokine, a monokine, a growth factor, an enzyme or a hormone;
  iv) an immunomodulatory gene;
  v) a gene encoding a cytotoxic polypeptide; and,
  vi) a suicide gene;
b) a cytotoxin;
c) a radionuclide;
d) a pro-drug; and
e) a therapeutic nucleic acid.

2. The method of claim 1, wherein said therapeutic agent is chemically coupled to said pseudovirus or said VLP.

3. The method of claim 1, wherein said therapeutic agent is incorporated within said pseudovirus or said VLP.

4. The method of claim 1, wherein said therapeutic agent is a toxin.

5. The method of claim 1, wherein said therapeutic agent is ganciclovir or acyclovir.

6. The method of claim 1, wherein said therapeutic agent is oligo T or a nucleic acid expressing oligo T.

7. The method of claim 6, wherein said oligo T is less than or equal to 200, 175, 150, 125, 100, 95, 80, 75, 70, 65, 60, 55, 50, 45, 40, 35, 30, 25, 20, 15, or 10 nucleotides.

8. The method of claim 1, wherein said therapeutic agent is a nucleic acid expressing oligo T and said nucleic acid is operably joined to a Pol III promoter.

9. The method of claim 1, wherein said therapeutic agent is a radionuclide.

* * * * *